(12) United States Patent
Callahan et al.

(10) Patent No.: US 8,764,664 B2
(45) Date of Patent: Jul. 1, 2014

(54) METHODS AND APPARATUS FOR CONFORMABLE MEDICAL DATA ACQUISITION PAD AND CONFIGURABLE IMAGING SYSTEM

(75) Inventors: Karla M. Callahan, Campbell, CA (US); Firat Kahraman, Campbell, CA (US)

(73) Assignee: Vizyontech Imaging, Inc., San Jose, CA (US)

( * ) Notice: Subject to any disclaimer, the term of this patent is extended or adjusted under 35 U.S.C. 154(b) by 1546 days.

(21) Appl. No.: 11/562,951

(22) Filed: Nov. 22, 2006

(65) Prior Publication Data

US 2007/0167782 A1    Jul. 19, 2007

Related U.S. Application Data

(60) Provisional application No. 60/740,175, filed on Nov. 28, 2005.

(51) Int. Cl.
*A61B 8/14* (2006.01)

(52) U.S. Cl.
USPC ............ 600/459; 600/447; 367/140; 73/596; 310/300

(58) Field of Classification Search
USPC ................. 600/447, 459; 367/140; 73/596
See application file for complete search history.

(56) References Cited

U.S. PATENT DOCUMENTS

| | | |
|---|---|---|
| 3,833,825 A | 9/1974 | Haan |
| 5,003,965 A | 4/1991 | Talish et al. |
| 5,164,920 A | 11/1992 | Bast et al. |
| 5,335,663 A | 8/1994 | Oakley et al. |
| 5,379,769 A | 1/1995 | Ito et al. |
| 5,408,703 A | 4/1995 | Cicio |
| 5,415,175 A | 5/1995 | Hanafy et al. |
| 5,437,283 A | 8/1995 | Ranalletta et al. |
| 5,469,853 A | 11/1995 | Law et al. |
| 5,485,842 A | 1/1996 | Quistgaard |
| 5,527,741 A | 6/1996 | Cole et al. |

(Continued)

FOREIGN PATENT DOCUMENTS

WO    WO 98/29036 A1    7/1998

OTHER PUBLICATIONS

European search report dated May 6, 2010 for Application No. 6838536.8.

(Continued)

*Primary Examiner* — Unsu Jung
*Assistant Examiner* — Joseph M Santos Rodriguez
(74) *Attorney, Agent, or Firm* — Wilson, Sonsini, Goodrich & Rosati

(57) ABSTRACT

A conformable medical data acquisition pad and configurable imaging system. The conformable pad may comprise a carrier base having a plurality of transceivers in operative association with an interconnection network that communicates with a computer system. The data acquisition pad may be constructed with a flex circuit and at least one ultrasound data collection device to carry out a variety of medical procedures. Different types of signal transmitting and receiving elements can be selected to provide ultrasound systems, including scalable capacitive micromachined ultrasound transducers arranged in a variety of configurations in combination with controlling electronics which interface with a translator board and software for signal processing. The resulting ultrasound data, such as a three-dimensional model, can be transmitted via an industry standard high speed bus to standard interfaces on various ultrasound systems.

11 Claims, 31 Drawing Sheets

(56) References Cited

U.S. PATENT DOCUMENTS

| | | | |
|---|---|---|---|
| 5,529,070 A | 6/1996 | Augustine et al. | |
| 5,556,372 A | 9/1996 | Talish et al. | |
| 5,562,095 A | 10/1996 | Downey et al. | |
| 5,574,212 A | 11/1996 | Madsen et al. | |
| 5,590,659 A | 1/1997 | Hamilton et al. | |
| 5,595,179 A | 1/1997 | Wright et al. | |
| 5,603,327 A | 2/1997 | Eberle et al. | |
| 5,671,746 A * | 9/1997 | Dreschel et al. | 600/472 |
| 5,680,865 A | 10/1997 | Tanaka | |
| 5,713,831 A | 2/1998 | Olsson | |
| 5,782,767 A * | 7/1998 | Pretlow, III | 600/443 |
| 5,806,521 A | 9/1998 | Morimoto et al. | |
| 5,865,733 A | 2/1999 | Malinouskas et al. | |
| 5,870,351 A | 2/1999 | Ladabaum et al. | |
| 5,894,452 A | 4/1999 | Ladabaum et al. | |
| 5,947,905 A | 9/1999 | Hadjicostis et al. | |
| 5,971,923 A | 10/1999 | Finger | |
| 5,997,479 A | 12/1999 | Savord et al. | |
| 6,017,311 A | 1/2000 | Sakamoto | |
| 6,049,158 A | 4/2000 | Takeuchi et al. | |
| 6,126,602 A | 10/2000 | Savord et al. | |
| 6,226,228 B1 | 5/2001 | Hossack et al. | |
| 6,261,231 B1 | 7/2001 | Damphousse et al. | |
| 6,359,367 B1 | 3/2002 | Sumanaweera et al. | |
| 6,425,870 B1 | 7/2002 | Flesch | |
| 6,432,070 B1 | 8/2002 | Talish et al. | |
| 6,440,071 B1 | 8/2002 | Slayton et al. | |
| 6,440,072 B1 | 8/2002 | Schuman et al. | |
| 6,443,901 B1 | 9/2002 | Fraser et al. | |
| 6,468,218 B1 | 10/2002 | Chen et al. | |
| 6,537,219 B2 | 3/2003 | Poland et al. | |
| 6,569,097 B1 | 5/2003 | McMorrow et al. | |
| 6,582,371 B2 | 6/2003 | Miller | |
| 6,582,372 B2 | 6/2003 | Poland | |
| 6,605,043 B1 | 8/2003 | Dreschel et al. | |
| 6,673,018 B2 | 1/2004 | Friedman | |
| 6,780,154 B2 * | 8/2004 | Hunt et al. | 600/446 |
| 6,817,982 B2 | 11/2004 | Fritz et al. | |
| 6,821,729 B2 | 11/2004 | Ackley et al. | |
| 6,826,816 B2 | 12/2004 | Emery et al. | |
| 6,891,311 B2 | 5/2005 | Phelps et al. | |
| 6,919,508 B2 | 7/2005 | Forcier | |
| 6,930,494 B2 | 8/2005 | Tesdahl et al. | |
| 6,969,352 B2 | 11/2005 | Chiang et al. | |
| 6,973,342 B1 | 12/2005 | Swanson | |
| 6,994,674 B2 | 2/2006 | Sheljaskow et al. | |
| 7,012,017 B2 | 3/2006 | Brunner et al. | |
| 7,037,264 B2 | 5/2006 | Poland | |
| 7,057,889 B2 | 6/2006 | Mata et al. | |
| 7,066,887 B2 | 6/2006 | Flesch et al. | |
| 7,087,023 B2 | 8/2006 | Daft et al. | |
| 7,115,093 B2 | 10/2006 | Halmann et al. | |
| 7,125,387 B2 | 10/2006 | Kawabata et al. | |
| 7,129,721 B2 | 10/2006 | Hamren et al. | |
| 7,798,970 B2 * | 9/2010 | Lo et al. | 600/459 |
| 2001/0041842 A1 | 11/2001 | Eberle et al. | |
| 2002/0075383 A1 | 6/2002 | Trobaugh et al. | |
| 2002/0111568 A1 | 8/2002 | Bukshpan et al. | |
| 2002/0156414 A1 | 10/2002 | Redding, Jr. | |
| 2002/0193708 A1 | 12/2002 | Thompson et al. | |
| 2003/0135135 A1 | 7/2003 | Miwa et al. | |
| 2003/0138187 A1 * | 7/2003 | Kawase et al. | 385/14 |
| 2003/0144611 A1 | 7/2003 | Coffey et al. | |
| 2003/0153849 A1 | 8/2003 | Huckle et al. | |
| 2004/0000847 A1 | 1/2004 | Ladabaum et al. | |
| 2004/0153009 A1 | 8/2004 | Horzewski et al. | |
| 2004/0167409 A1 * | 8/2004 | Lo et al. | 600/485 |
| 2004/0256959 A1 | 12/2004 | Ladabaum | |
| 2005/0099089 A1 * | 5/2005 | Baumgartner | 310/311 |
| 2005/0119575 A1 | 6/2005 | Ladabaum et al. | |
| 2005/0146240 A1 | 7/2005 | Smith et al. | |
| 2005/0146247 A1 | 7/2005 | Fisher et al. | |
| 2005/0177045 A1 * | 8/2005 | Degertekin et al. | 600/457 |
| 2005/0203409 A1 * | 9/2005 | Frey et al. | 600/459 |
| 2005/0225916 A1 | 10/2005 | Bolorforosh et al. | |
| 2005/0228277 A1 | 10/2005 | Barnes et al. | |
| 2006/0125348 A1 | 6/2006 | Smith et al. | |
| 2006/0230835 A1 | 10/2006 | Wang | |
| 2006/0241522 A1 | 10/2006 | Chandraratna | |

OTHER PUBLICATIONS

International search report dated Sep. 25, 2007 for PCT Application No. US2006/45627.

Daft, et al. cMUTs and electronics for 2D and 3D imaging: monolithic integration, in-handle chip sets and system implications. 2005 IEEE Ultrasonics Symposium. 2005; 1:463-474.

\* cited by examiner

METHODS AND APPARATUS FOR CONFORMABLE MEDICAL DATA ACQUISITION PAD AND CONFIGURABLE IMAGING SYSTEM

This application claims the benefit of U.S. Provisional Application No. 60/740,175, filed Nov. 28, 2005, which is incorporated herein by reference in its entirety.

BACKGROUND OF THE INVENTION

Ultrasonic diagnostic imaging systems are in widespread use for performing ultrasonic imaging and measurements. For example, cardiologists, radiologists, and obstetricians use ultrasonic diagnostic imaging systems to examine the heart, various abdominal organs, or a developing fetus, respectively. In general, imaging information is obtained by these systems by placing an ultrasonic probe against a transmission agent such as a liquid gel and the skin of a patient, and actuating an ultrasonic transducer located within the probe to transmit ultrasonic energy through the skin and into the body of the patient. In response to the transmission of ultrasonic energy into the body, ultrasonic echoes emanate from the interior structure of the body. The returning acoustic echoes are converted into electrical signals by the transducer in the probe, which are transferred to the diagnostic system by a cable coupling the diagnostic system to the probe.

Acoustic transducers commonly used in ultrasonic diagnostic probes are often comprised of an array of individual piezoelectric elements. These elements are usually formed from a piezoelectric material by the following a number of meticulous manufacturing steps. In one common method, a piezoelectric transducer array is formed by bonding a single block of piezoelectric material to a backing member that provides acoustic attenuation. The single block is then laterally subdivided by cutting or dicing the material to form the rectangular elements of the array. Electrical contact pads are formed on the individual elements using various metallization processes to permit electrical conductors to be coupled to the individual elements of the array. The electrical conductors are then coupled to the contact pads by a variety of electrical joining methods, including soldering, spot-welding, or by adhesively bonding the conductor to the contact pad.

Although current methods such as the foregoing are generally adequate to form acoustic transducer arrays having up to a few hundred elements, larger arrays of transducer elements having smaller element sizes are not as easily formed using these approaches. Consequently, various techniques used in the fabrication of silicon microelectronic devices have been adapted to form ultrasonic transducer elements, in part because these techniques generally permit the repetitive fabrication of small structures in intricate detail.

An example of a device that may be formed using semiconductor fabrication methods is a micro-machined or micro-fabricated ultrasonic transducer (MUT). The MUT has several significant advantages over conventional piezoelectric ultrasonic transducers. For example, the structure of the MUT generally offers more flexibility in terms of optimization parameters than is typically available in conventional piezoelectric devices. Further, the MUT may be conveniently formed on a semiconductor substrate using various semiconductor fabrication methods, which advantageously permits the formation of relatively large numbers of transducers. The formation of numerous transducers may then be integrated into providing large transducer arrays. Additionally, interconnections between MUTs in arrays and the electronic devices external to the arrays may also be conveniently formed during the fabrication process. MUTs may be operated capacitively, and are commonly referred to as cMUTs, as shown in U.S. Pat. No. 5,894,452, which is incorporated by reference herein in its entirety. Alternatively, piezoelectric materials may be used in fabrication of MUTs, which are commonly referred to as pMUTs, as shown in U.S. Pat. No. 6,049,158, which is incorporated by reference herein in its entirety. Accordingly, MUTs have increasingly become an attractive alternative to conventional piezoelectric ultrasonic transducers in ultrasound systems.

Furthermore, some ultrasound devices available today utilize multiple, individual transducer elements supported by quilt-like substrates. See U.S. Pat. App. Pub. No. 2006/0241522, which is incorporated by reference herein in its entirety. Such materials in these devices may not provide adequate ultrasound transmission efficiency or satisfactory imaging resolution.

There is a need for instrumentation and procedures capable of obtaining ultrasound images and other types of medical data information using a coordinated interconnected network of micro-fabricated elements that can be manufactured efficiently and in a cost effective manner.

SUMMARY OF THE INVENTION

The invention provides data acquisition methods and apparatus for obtaining a wide variety of medical information. In preferable embodiments of the invention, ultrasound imaging systems and related methods of their use are provided that include configurable scanning devices that can be modified for certain applications. The scanning devices may include ultrasound probes and pads that can be configured into different physical forms (e.g., flat, strip, cone) that can be either structurally flexible or relatively fixed for selected portions of the patient anatomy.

Various aspects of the invention described herein for other purposes and procedures relating to ultrasound or imaging applications are equally applicable to other medical procedures involving data acquisition. To the extent such descriptions relate to steps and apparatus for imaging and application of ultrasound technology, the same can be equally applied and interchangeable with such other medical procedures. It shall be understood that different aspects of the invention can be appreciated individually, collectively or in combination with each other.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The following is a description of various embodiments of the invention illustrated in the accompanying drawings.

It shall be noted that corresponding reference characters may indicate corresponding elements among and between the various figures or drawings herein. The headings used in the accompanying figures should not be interpreted to limit the scope of the invention with respect to such figures only.

DETAILED DESCRIPTION OF THE INVENTION

Figure 1:
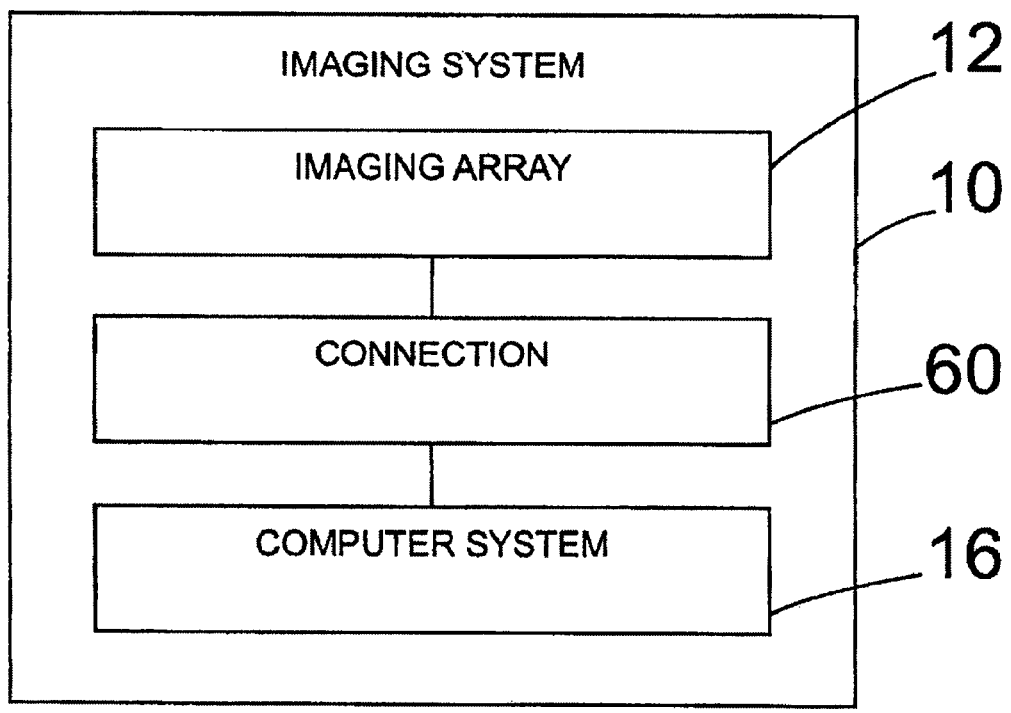
FIG. 1 is a simplified block diagram illustrating a data acquisition, therapy and/or imaging system.

FIG. 1 illustrates an implementation of an imaging system 10 provided in accordance with an aspect of the invention that includes an imaging array 12. The imaging system 10 can generate a variety of medical data, hereinafter encompassed by the general term "image data" on an area of concern of a subject, such as patient, using an imaging array 12 in operative association with a translator board and/or computer system 16 through a connection 60.

In one embodiment of the invention, the area of concern may be selected at the time of imaging from a variety of body tissues, organs and structures. In other embodiments, the area of concern may be predetermined such that the imaging system 10 may be targeted for a specific body tissue, organ or structure such as the breast, sinuses or skin. In another embodiment, the areas of concern may be targeted for a range of related medical specialties such as gynecology that may include the breast, the pelvic area and/or surrounding region. Others areas of concern on a variety of subjects are also contemplated.

The dimensions and size of the imaging array 12 may depend on the application for which the imaging array 12 is used. For example, an imaging array designed for specific point skin imaging may be much smaller than an imaging array designed for abdominal organ imaging.

In another embodiment of the invention, the imaging array 12 may be structurally flexible, while in another embodiment the imaging array 12 may be rigid. The imaging array 12 may also fully or partially conform to an area of concern that is being analyzed. Moreover, the imaging array 12 may be of a designated size, flexibility and conformity for a particular type of reading. Several implementations of various imaging arrays provided in accordance with this aspect of the invention are described in greater detail below.

Figure 2:
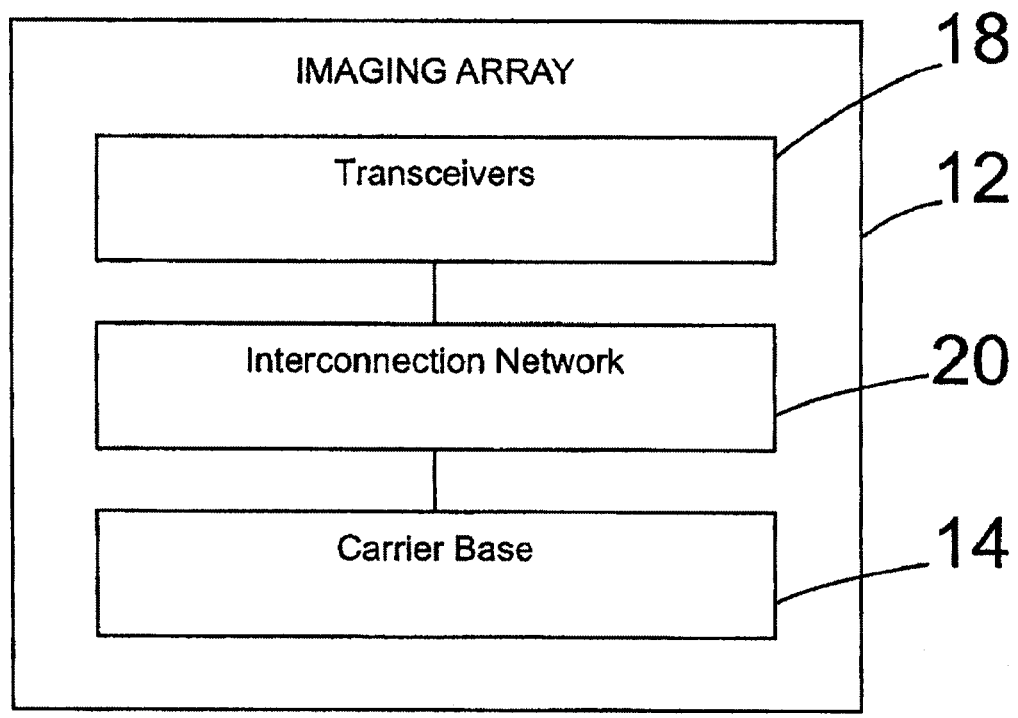
FIG. 2 is a simplified block diagram illustrating a data acquisition and/or imaging array, hereinafter referred to as an imaging array.

The imaging array 12 illustrated in FIG. 2 may include a carrier base 14 having groups or clusters of one or more transceivers 18 that are in operative association with a computer system 16 through an interconnection network 20. The interconnection network may include electrical and thermal materials and components that are active or passive, integral to one another, distributed or modular, for example, on a separate printed circuit board. The carrier base 14 may be manufactured from a flexible fabric and act as a flexible base. Several implementations of the carrier base 14 are described in greater detail below. In addition, the interconnection network 20 may operatively interconnect each transceiver 18 with the computer system 16 to provide power and communication functions for imaging system 10. In one preferable embodiment of the invention, each transceiver 18 may have the capability to receive independent electrical signals and be electrically isolated, and in another embodiment, each transceiver 18 may be connected to one or more other transceivers 18.

A preferable embodiment of the invention includes an interconnection 20 that can include a multilevel or multilayer network to achieve electrical isolation of signals such that each transceiver 18 may functional independent of all other transceivers 18. In a more preferable embodiment, such electrical isolation may be achieved by insulating the electrically conductive network pathways for each transceiver 18 from one another. The various electrical connections for the transceivers 18 herein and the input/output control (shown as one or more terminal ends 44) may be patterned and incorporated into or onto the carrier base 14. The electrical connections may be connected to computer system 16 either wirelessly or with connective wiring/cables.

One or more of the transceivers, used herein as a term inclusive of a variety of sensors detailed below, 18 may be a device capable of both transmitting an analysis signal and receiving a detection signal. In a preferable embodiment of the invention, the detection signal received by selected transceivers 18 may be the echo of the analysis signal, such as in the case of ultrasound analysis. In an alternative embodiment of the invention, one or more transceivers 18 may be a device capable of transmitting infrared as an analysis signal and receiving a detection signal in the form of residual temperature or heating assessment. In yet another embodiment of the invention, one or more transceivers 18 may be a device capable of generating an electromotive field for movement of chemical components and receiving a detection signal in the form of subcutaneous electrical conductivity.

According to another aspect of the invention, the analysis signal and the detection signal from a transceiver may be used for obtaining imaging data to be used for multiple purposes. The imaging data may be preferably used to form an image, but in other embodiments of the invention the analysis signal and the detection signal may be used for obtaining imaging data to perform an analysis or interpretation directly for therapy decision, guidance, analysis and follow-up. In addition, the imaging data may also be used for diagnosis, analysis, determining concentration of chemicals, radiation dosing, treating an area and therapy such as delivering heat or electromotive movement of medication through skin or other tissue, placement targeting for radiation therapy, and guided procedures such as biopsy or surgery.

Different kinds of signals may be transmitted and/or received by the transceivers provided herein. The analysis signals and the detection signals from a transceiver may be ultrasound signals, while in another embodiment the analysis signals and the detection signals may be infrared signals. However, other kinds of medically related analysis signals and detection signals are also contemplated herein in accordance with this aspect of the invention.

Furthermore, in a preferable embodiment of the invention, the transceivers 18 may be devices that both transmit analysis signals and receive detection signals. However, in alternative embodiment, a distinct transmitter and receiver arrangement may also be used to transmit analysis signals and receive detection signals using separate devices to accomplish the same or substantially similar results. In one alternate embodiment of the invention, each transceiver 18 may be capable of transmitting and receiving a wide variation of frequencies. The combination of transceiver designs may also allow simultaneous therapy and imaging or data acquisition.

In another embodiment of the invention, the selected transceivers 18 may be silicon-based solid-state transceivers. The silicon-based solid-state transceivers may be into the category of micro-electro-mechanical systems (MEMS). Another example of a MEMS type device that may be used in accordance with this embodiment include a capacitive micromachined ultrasound transducer (cMUT). These cMUTs may include metallized membranes (forming the top electrode) suspended above heavily doped silicon bulk (forming a bottom electrode). An example of a producer of MEMS may be Honeywell, Innovative Microtechnologies or Micralyne Inc. Other embodiments of the invention herein may incorporate the use of transducer elements such as piezoelectric transducers (such as, but not limited to, PZTs).

In yet another embodiment of the invention, the transceivers 18 may be silicon-based integrated circuit transceivers. In a more preferable embodiment, the silicon-based integrated circuit transceivers may be micro-electronic in design. And in yet another embodiment, the transceivers 18 may be made from piezoelectric crystal materials.

It shall be understood that for the various embodiments of the invention herein, each transceiver 18 may be conceptualized as or represent an entire transceiver array itself, while in other embodiments each described transceiver 18 may be a discrete single transceiver. Other embodiments having differing numbers and configurations of each transceiver 18 are also contemplated.

It should be appreciated that varying number of transceivers 18 may be used and located at different positions of an imaging array 12 in various embodiments of the invention. The transceivers 18 may be attached to a carrier base 14 to facilitate connection both physically and electrically.

In one alternative embodiment, a position sensor (not shown) may be included on imaging array 12 to record the position of imaging array 12 during a scan, such as when imaging array 12 may move during a reading, a patient may move during a reading, or carrier base 14 may be curved. The position sensor may be an accelerometer, a redundant overlay, sense-and-receive, or MiniBird, LaserBird or Flock of Birds type of position sensors produced by Ascension Technology Corporation, the Fastrak produced by Polhemus and the Polaris produced by Northern Digital; however other position sensors are also contemplated.

As shown in FIGS. 1 and 2, an imaging array 12 may be connected to computer system 16 through connection 60 for a variety of purposes including control and analysis of the ultrasound image generation, three-dimensional presentation, medical diagnostic analysis and visual creation. Data and signals may be transmitted from the imaging array 12 to a computer system 16 through a wired connection (e.g., a cable) such as through an electrical or optical transmission or wirelessly.

Figure 3A:
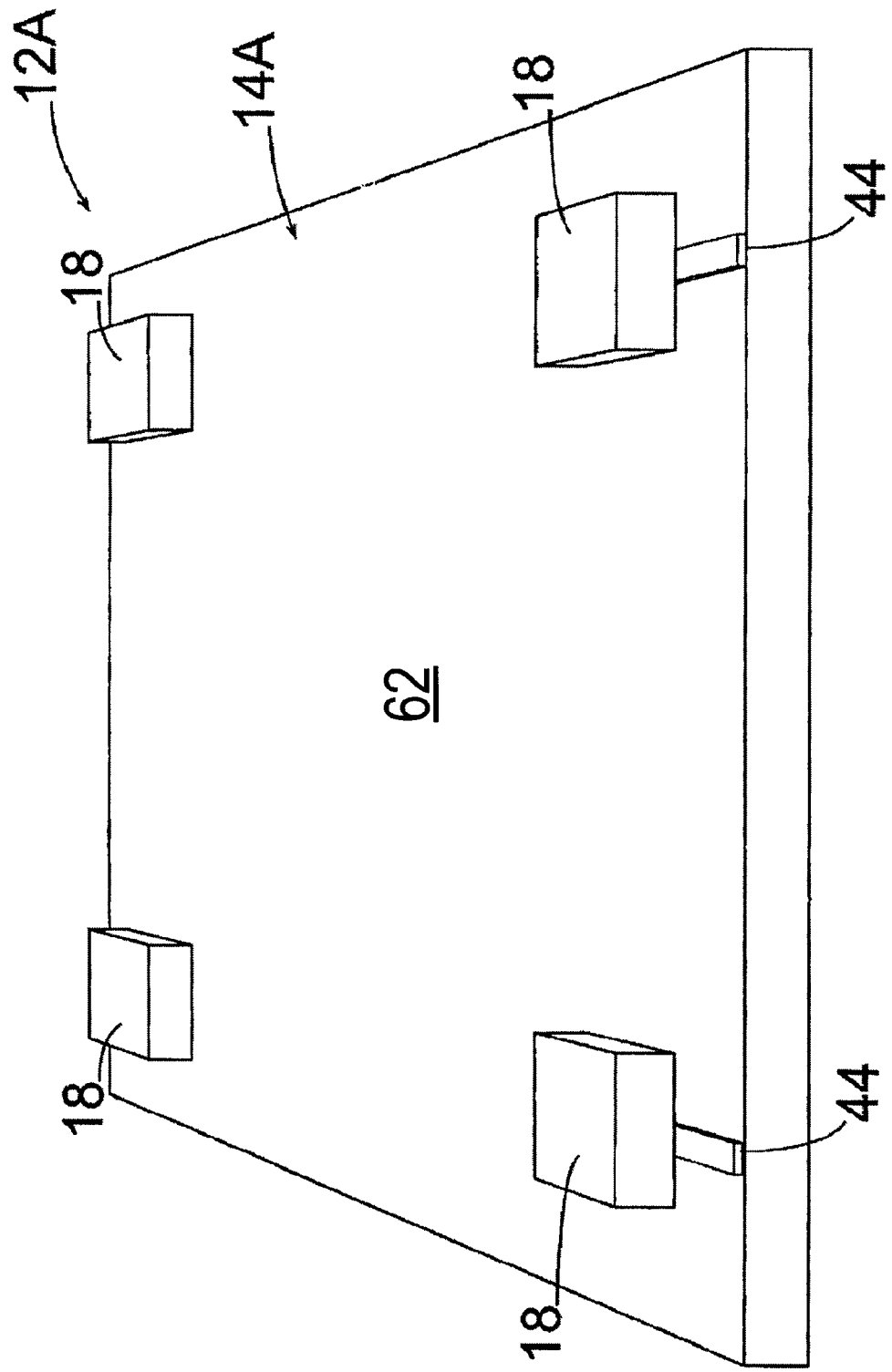
FIG. 3A is a simplified perspective view showing an imaging array having a ceramic fabric-like or rigid carrier base.

In a preferable embodiment of the invention where a cable connection may be used to connect an imaging array 12 to a computer system 16, a connector device (not shown) may facilitate joining one or more terminal ends (see FIG. 3A (44)) of a series of one or more transducers or transceivers to a joining coupler device (not shown) that interfaces with the cable connect to carry signals to and from computer system 16, with the computer system being housed in one contiguous configuration or in a distributed or modular configuration operatively working together.

In another alternative embodiment, a wireless connection may be used to connect an imaging array 12 to a computer system 16. A connector device may facilitate joining one or more terminal ends, e.g., FIG. 3A (44), of a series of one or more transducers or transceivers to a communication device (now shown) that interfaces with the computer system 16.

In yet another alternative embodiment, the imaging system 10 may transmit imaging data to a remote computer system (not shown) separate from the imaging system, while in another embodiment the imaging system may process the imaging data using an intermediate circuit board, such as the image processing board from Terarecon, application specific integrated circuit (ASIC) or chip-set or a computer system 16 that is integral to and local to the imaging system.

As with other embodiments of the invention herein, a gel-like material described in greater detail below may be incorporated into or onto a carrier base 14 and the series of one or more transceivers 18 to eliminate the need to use of a liquid transmission gel. The dimensions of the carrier base 14 and placement of the transceivers 18 may be oriented for specific end-use applications and body part imaging. In a preferable embodiment, a computer system 16 as described in greater detail below may include hardware and/or software to provide a visual image and three-dimensional orientation of a part of a body of a patient being imaged. Other implementations of such a computer system 16 are described in greater detail below.

Referring to FIG. 3A, an implementation of the invention is illustrated that provides an imaging array 12. The imaging array, designated 12A, may include a carrier base 14A made from a carrier material such as ceramic materials to provide a ceramic layer that defines a surface area 62. The group of one or more transceivers 18 may be positioned on the surface area 62 of the carrier base 14A with an interconnection network such as those described elsewhere herein, e.g., FIG. 2 (20), which is in operative association with each transceiver 18. It shall be understood that other data acquisition elements such as transducers may be selected instead to provide alternative embodiments of the invention herein.

In a preferable embodiment of the invention, the interconnection network may be manufactured using a thick film paste process or a metal foil process. However, metal evaporation techniques may also be used to provide an interconnection network such as filament evaporation, electron-beam evaporation, flash evaporation, induction evaporation, and sputtering. Other suitable methods, particularly those employed in semiconductor processing, may be used in manufacturing the interconnection networks herein which are also contemplated in accordance with the invention.

A group of one or more terminal ends 44 as shown in FIG. 3A may be electrically connected as part of an imaging array to allow the transmission of signals, data and communication with a receiving computer system, e.g., FIG. 1 (16). This connection may be wireless or with physical wires, cables, light fiber, etc. The terminal ends 44 can be insulated and isolated to maintain independent signal integrity into a connector device.

With respect to any of the embodiments of the invention herein, the selected carrier material may be a ceramic material including flexible ceramic fabrics. A variety of suitable ceramic fabrics include those manufactured by 3M Corporation such as 3M Nextel Woven Fabric 610. It should be appreciated that such fabric may be sized as needed depending on application of imaging array 12.

Figure 3B:
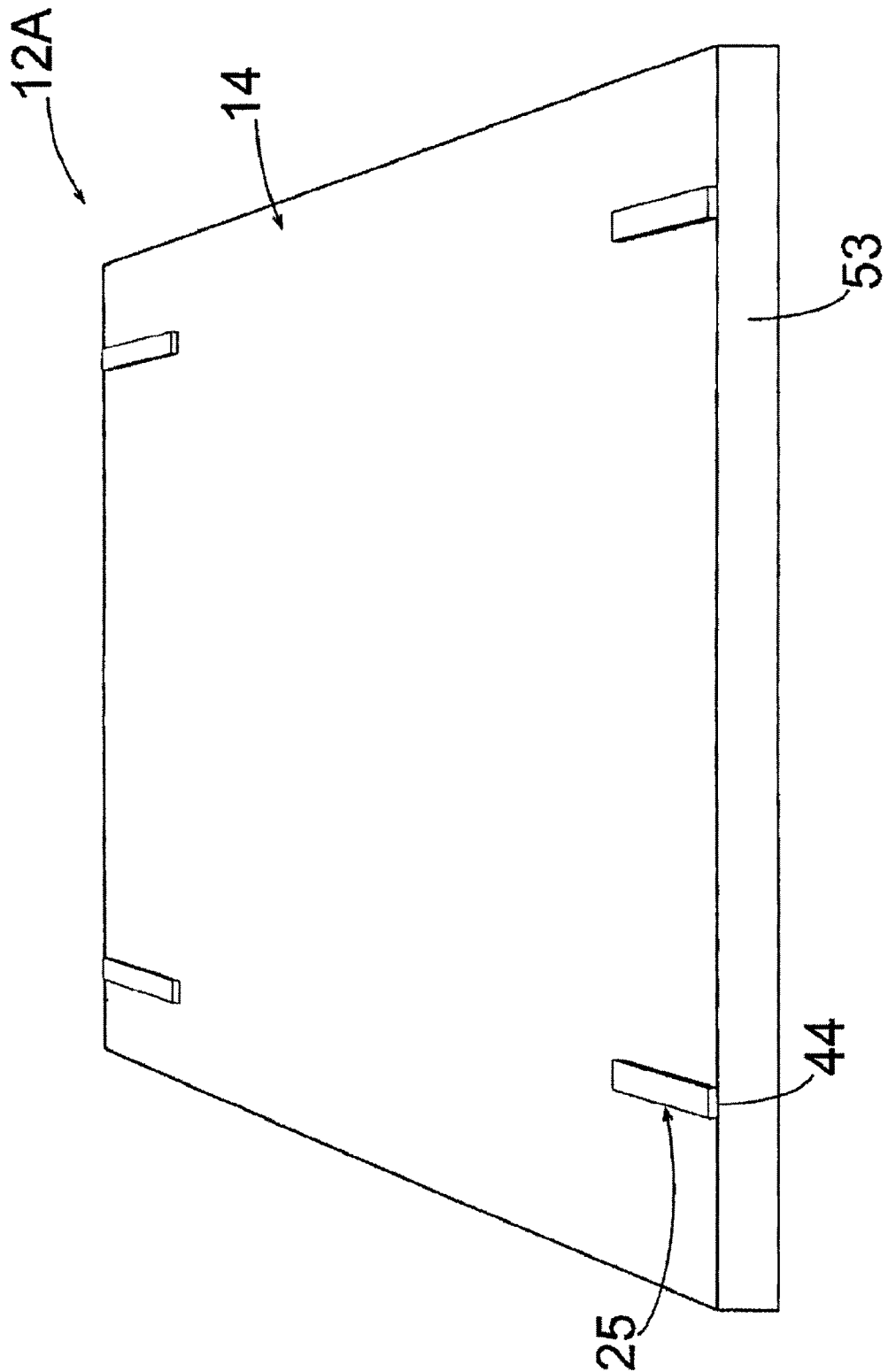
FIG. 3B is the simplified perspective view of an imaging array shown in FIG. 3A without the transceivers showing the interconnection network of the imaging array on the ceramic carrier base.

Referring to FIG. 3B, an imaging array 12A provided in accordance with the invention is shown without transceivers, e.g., FIG. 3A (18), to further illustrate the series of one or more underlying terminal ends 44 corresponding to the transceivers. An interconnection network may be added thereon which includes interconnects, e.g., FIG. 3C (20B) in communication with each transceiver at one end, and conductive pathways 25 at the other end thereof. The conductive pathways 25 may include one or more terminal ends 44 adapted to establish an operative connection with a computer system through an selected kind of connection.

As with other embodiments of the invention herein, the imaging array 12A may be formed with a carrier base 14 using a single layer construction, while alternate embodiments provide imaging arrays formed using a multi-layer construction.

Figure 3C:
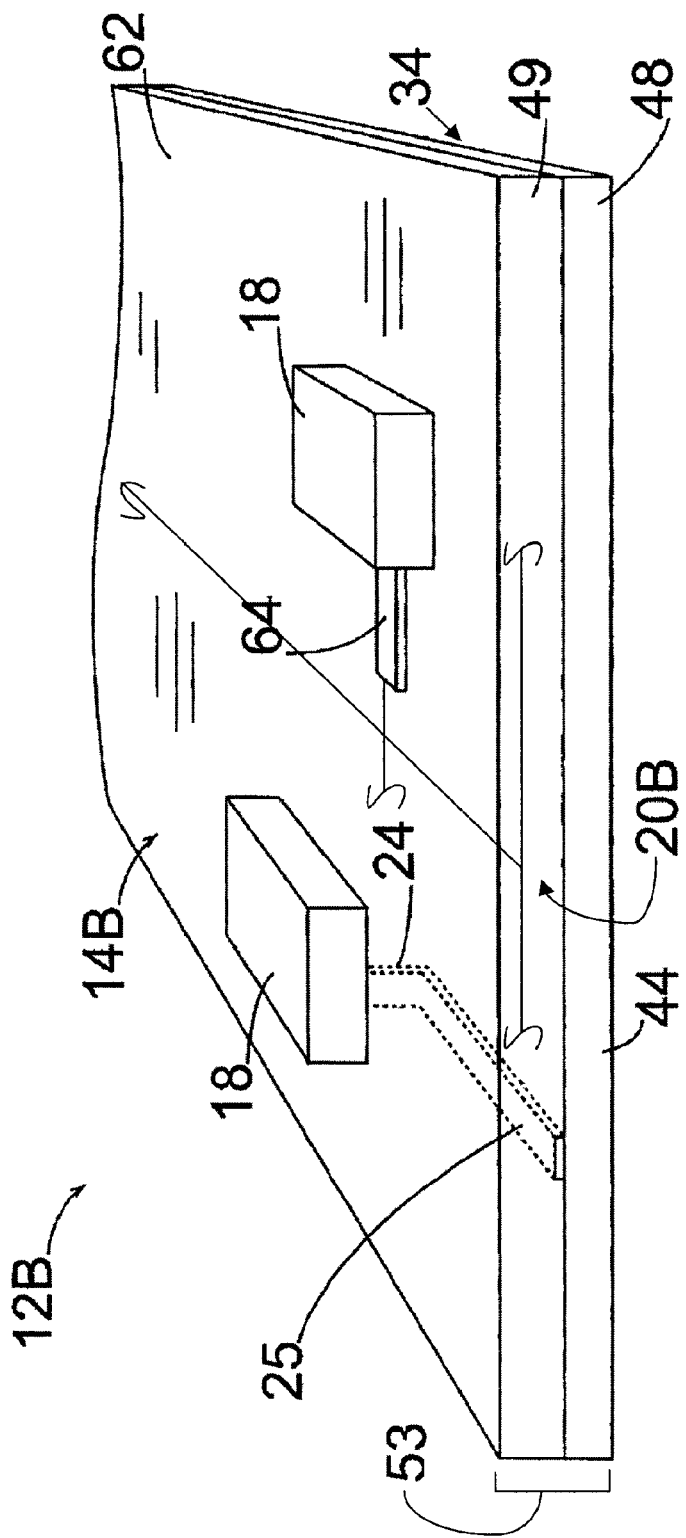
FIG. 3C is a simplified perspective view of an imaging array having the interconnect layer embedded in the ceramic carrier base.

Referring to FIG. 3C, an implementation of an imaging array 12B is illustrated which incorporates a multi- or dual layer construction. The imaging array 12B may include an interconnection network 20B substantially embedded inside a carrier base that can be formed of a ceramic layer 53 (shown as a first ceramic layer 48 and a second ceramic layer 49). The interconnection network 20B can be operatively engaged with each transceiver 18 which can remain positioned on a surface area 62 of the ceramic layer 53.

A plurality of interconnects 24 may be embedded inside the ceramic layer 53, while other interconnects may have a portion 64 located atop a selected portion of the surface area 62. As discussed above, the interconnects 24 may be operatively associated between conductive pathways 25 and each respective transceiver 18 with one or more terminal ends 44 positioned along one of the sides 34 of the ceramic layer 53. In one embodiment, the interconnects 24 may be formed of a metal material, however other compositions and deposition techniques may also be used, such as a thick film paste process. Moreover, other metal evaporation techniques may also be used to construct the interconnection networks used herein such as filament evaporation, electron-beam evaporation, flash evaporation, induction evaporation, and sputtering. Other suitable methods of manufacturing interconnection networks apparent to those of ordinary skill in the field are also contemplated herein.

Figure 4A:
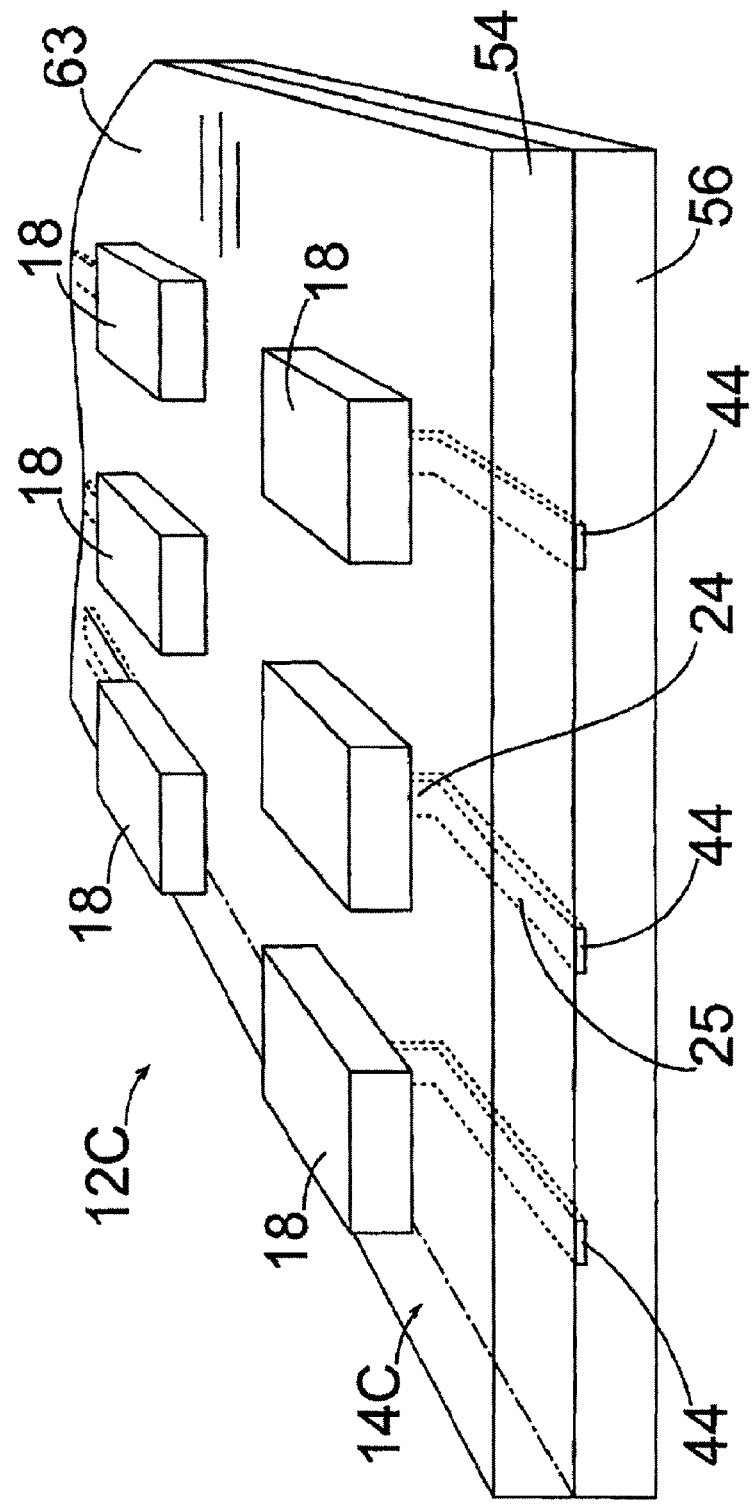
FIG. 4A is a simplified perspective view of an embodiment of an imaging array having an organic fabric carrier base.

Referring to FIG. 4A, another implementation of the invention is illustrated which provides an imaging array 12C. The imaging array 12C may include a carrier base 14C having a first organic layer 54 engaged to a second organic layer 56. The final number of layers can be determined based on the configuration of the imaging array based on the intended application. The first organic layer 54 may define a top surface area 63 having each of the transceivers 18 positioned thereon. The transceivers 18 may be in operative association or otherwise connected with an interconnection network as described elsewhere herein via corresponding interconnects 24 and conductive pathways 25 completely embedded in the carrier base 14C. In one configuration of the interconnection network, the conductive pathways 25 may have one or more terminal ends 44 wherein each terminal end 44 may be operatively connected to computer system, e.g., FIG. 1 (16).

In a preferable embodiment of the invention, the organic layer (e.g., first organic layer 54 and second organic layer 56) may be made from organic or polymeric materials such as polyimide, polyester, and polypropylene polymer compositions. Examples of organic layers that may be used in accordance with this embodiment of the invention include organic materials such as films, e.g., KAPTON polyimide and MYLAR polyester films (DuPont), that have metallized layers in the form of flex circuit or membrane circuits. . In a preferable embodiment of the invention, a polyimide film in flex circuit membrane style, may be used in combination with a conductive material, such as copper-based or carbon-based products, for constructing an interconnection network used in imaging arrays described herein. In yet another embodiment, a MYLAR polyester film may be used for further processing or to connect carrier base layers together by using processes that may include embossing, metallizing, printing on, stamping, punching, crimping and coating.

Figure 4B:
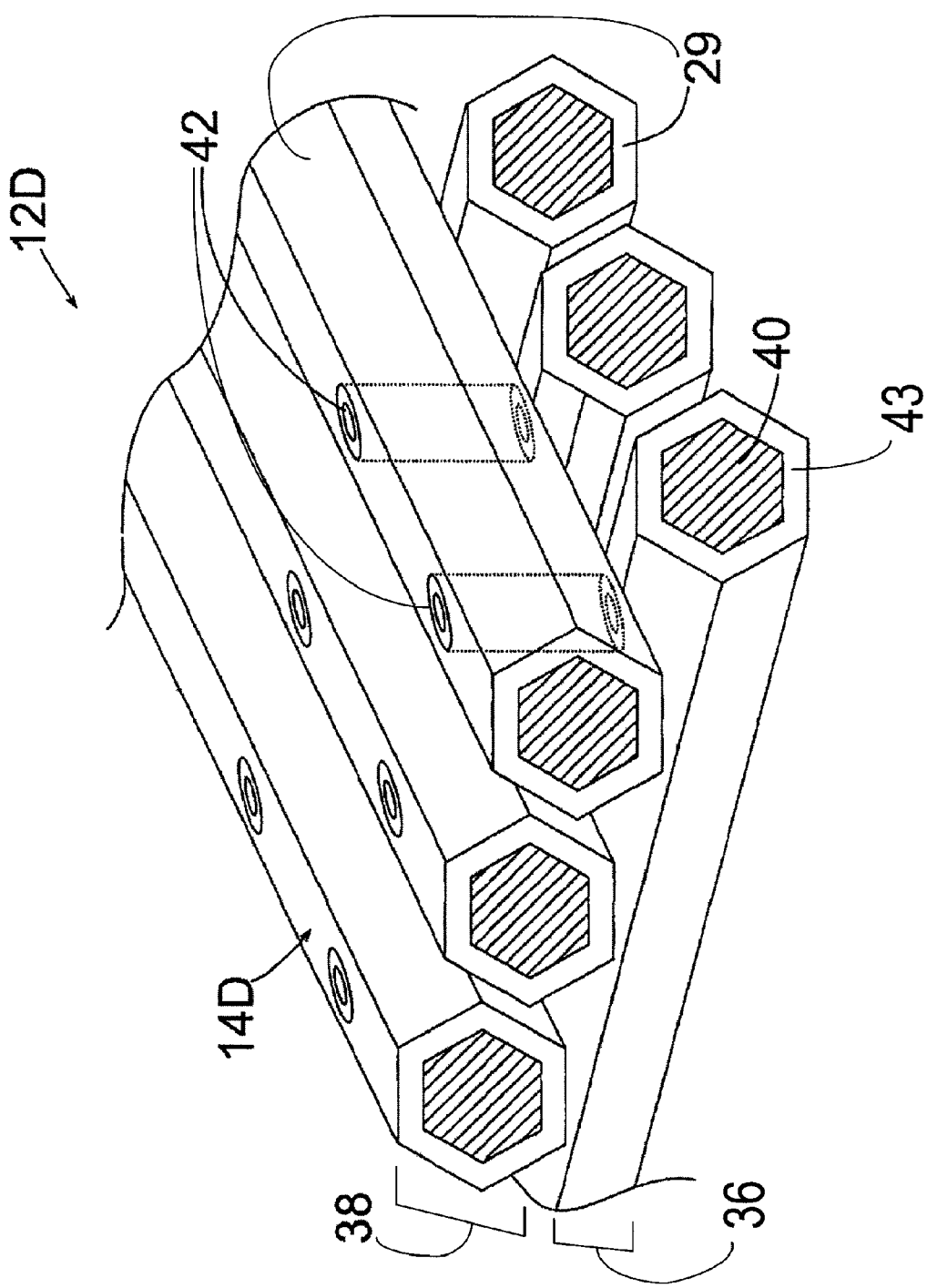
FIG. 4B is a perspective view of an imaging array having the organic fabric carrier base of elements.

Referring to FIG. 4B, another implementation of an imaging array 12D provided in accordance with the invention is illustrated. The imaging array 12D may include a carrier base 14D having a first element layer 36 and a second element layer 38. The first element layer 36 may include a series of one or more elements 29, while the second element layer 38 may also include a series of one or more elements 29. The elements aligned in the first element layer 36 may be positioned in a transverse orientation or perpendicular to the elements in the second element layer 38. As with other imaging arrays herein, an interconnect network (not shown) and attachment pads (not shown) may be positioned on top of the second layer 38 that contain terminal ends (not shown) (See FIG. 4A).

Each of the elements 29 may have a core 40 that is isolated from other cores of other elements. In a preferable embodiment, the cores 40 may be made from a carbon composite or other suitable conductive material, such as a solid metal core or a specially formulated or treated organic composition with conductive material integrated into the core. The elements 29 may have an organic cover 43 that defines or substantially surrounds a corresponding core 40. The organic covers 43 may be formed of a variety of polymeric and organic materials such as polypropylene, polyimide, polyamide, polyester, or other composites, however other organic materials may also be used.

In an alternative embodiment of the invention, each element 29 may include one or more vias 42 that act as connection points. The vias 42 may connect cores 40 from an element 29 located in the second element layer 38 to an element located within the first element layer 36. Furthermore, the vias 42 may be filled with conductive material to complete the selected connection electrically from one conductive path or level (layer) to the next adjoining path or level in either a vertically or horizontally manner to allow specific and isolated access to various locations of transceivers 18. An interconnection network (not shown) may be positioned on top of the second element layer 38 and may be connected to transceivers, transducers or other data acquisition elements described elsewhere herein through vias 42 The interconnection network may also serve for power and thermal distribution and control of electrical parameters such as impedance, inductance and cross-talk.

In a preferable embodiment of the invention, the elements 29 may be hexagonally shaped, however in other embodiments elements 29 may be round, oval, octagonal, and other regular and irregular shapes. The elements 29 may be the same shape or different shapes throughout an element layer.

Figure 5A:
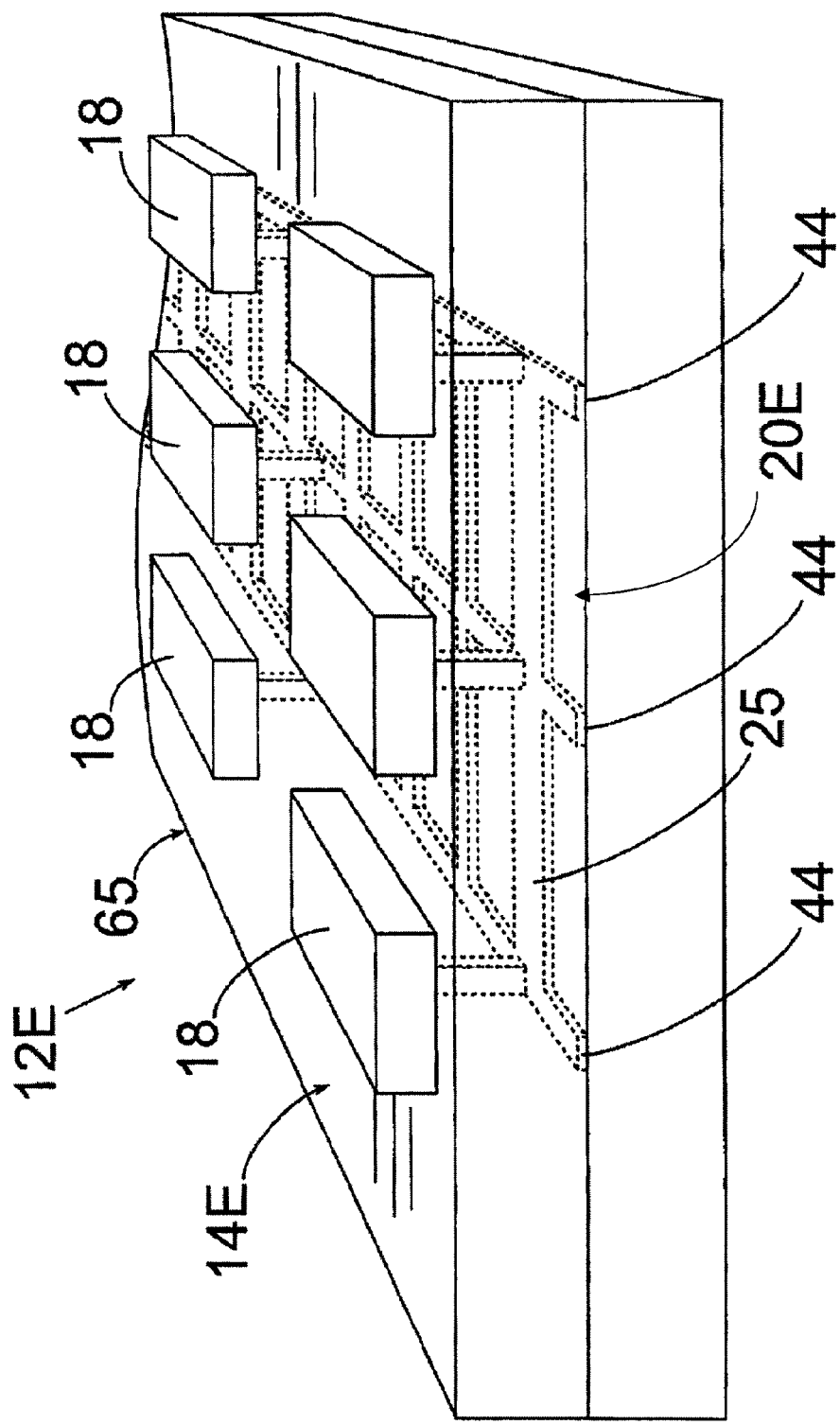
FIG. 5A is a simplified perspective view of an imaging array having a multi-layered carrier base made from a flex circuit membrane-like material and/or gel-like material.

Referring to FIG. 5A, another implementation of an imaging array 12E is illustrated in accordance with another aspect of the invention. The imaging array 12E may include a carrier base 14E made of a flex circuit membrane-like and/or a gel-like material. In a preferable embodiment, the gel-like material may include an interconnection network 20E embedded therein for operatively associating or communicating with a series of one or more transceivers 18 positioned on an outer surface 65 of the carrier base 14E. In another embodiment, the interconnection network 20E may be positioned on the surface of the flex circuit membrane-like and/or gel-like material. The carrier base 14E may be formed of a single layer or multiple layers of one or more different types of flex circuit and/or gel-like materials for application with other embodiments of the invention described elsewhere herein.

The interconnection network 20E may include one or more conductive pathways 25 in operative association with each transceiver 18. In one embodiment, the conductive pathway 25 may be made from a metal, carbon or other suitably electrically conductive material. The conductive pathway 25 may include one or more terminal ends 44 adapted to establish an operative and/or electrical connection with a computer system over a selected connection as described elsewhere herein.

In a preferable embodiment of the invention, the gel-like or other encapsulant material selected for the carrier base 14E may be a semi-solid gel that substantially maintains its general shape. The gel-like material may be an integral part of the carrier or it may be used to form a sleeve-like envelope into which the imaging array components fit. The basic composition of the gel-like material may include a silicone or polymer gel component with variations of additives to achieve optimum performance of the imaging array 12E in parameters such as transmission, frequency, power and impedance matching. The components of gel-like material may include silicone, water, propylene glycol, glycerin, phenoxyethanol, mineral oil, and coloring agents, although other components are also contemplated. For example, the gel-like material may also contain a combination of substances marketed as hydrators, which include jojoba oil, Vitamin E, olive oil, mineral oil and other similar nutrients. The gel-like material may be polymer gels marketed under the name SILIPOS, the SONTAC gel pad, or modified Sonic Blue standard gel (product number UP295, material safety designation MS71075 and UP298, MS71085) produced by Tyco Healthcare Group LP. It should be understood that other bio-compatible gel-like materials are also contemplated in accordance with this aspect of the invention. Furthermore, in alternative embodiments of the invention, the dimensions of carrier bases formed of gel-like material may vary from small areas just covering transceivers up to and including a single solid sheet. The gel-like materials that provide a top layer to cover the transceivers may be of a different composition from the gel-like material selected for a supporting bottom layer under the transceivers that together form carrier base to which transceivers are attached.

Figure 5B:
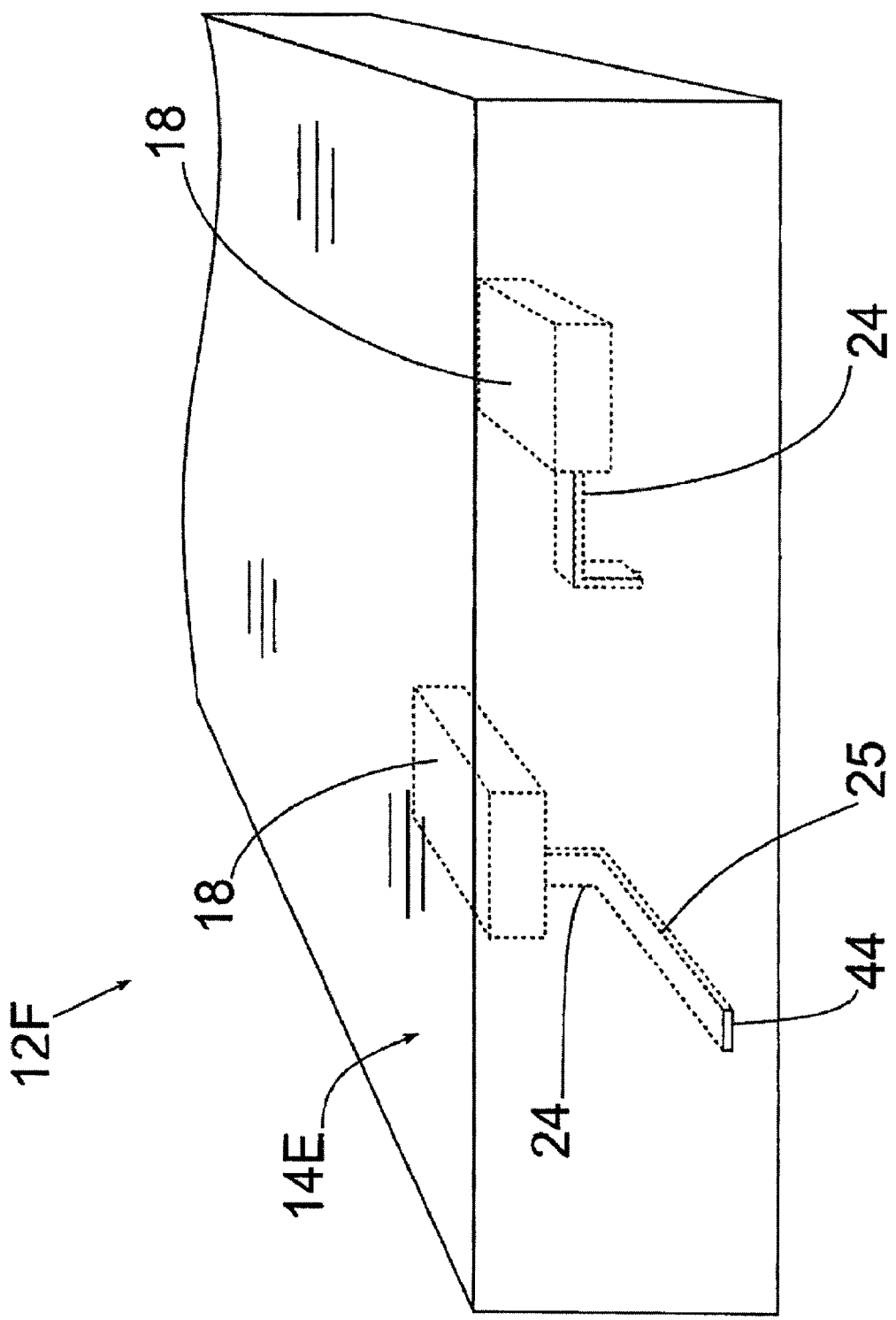
FIG. 5B is simplified perspective view of an imaging array having a single layer carrier base made from a gel-like material with the transceivers and interconnect layer embedded therein.

Referring to FIG. 5B, another implementation of an imaging array 12F is illustrated. In this implementation, the imaging array 12F may include a carrier base 14E made from flex circuit materials and/or gel-like material as noted above. However a group or cluster of transceivers 18 selected in this embodiment of the invention may be partially or completely embedded (encapsulated) within the gel-like material forming the carrier base 14E. In addition, a partially or completely embedded interconnection network (including interconnects 24, conductive pathways 25, and terminal ends 44) as described elsewhere herein may operatively associate or facilitate signal transmissions between each transceiver 18 and a computer system as described elsewhere herein.

Figure 5C:
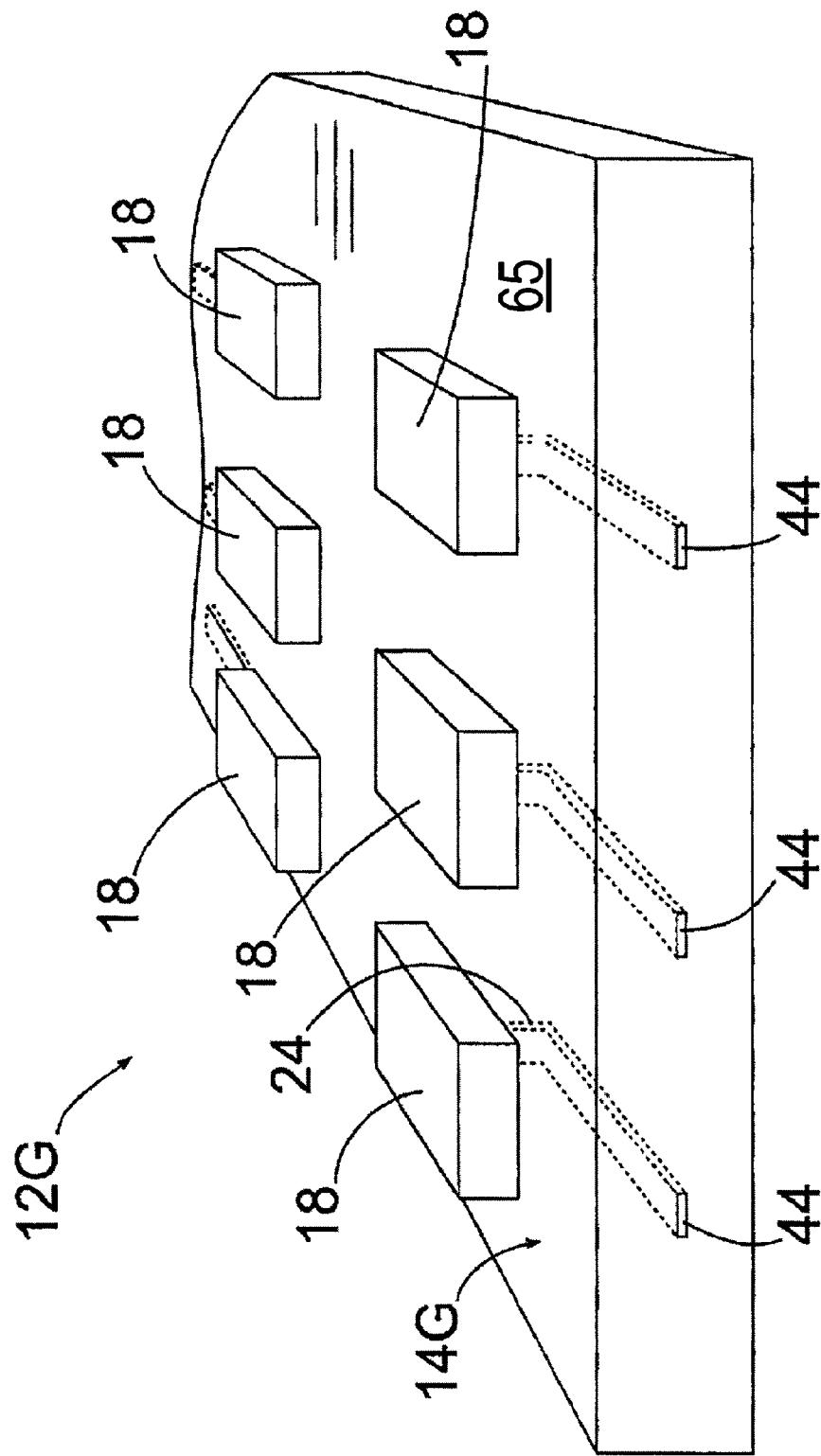
FIG. 5C is a simplified perspective view of an imaging array having a single layer carrier base made from a gel-like material with the interconnect layer embedded therein.

FIG. 5C illustrates yet another implementation an imaging array 12G that includes a carrier base 14G that can be made from the same or similar flex circuit-like and/or gel-like materials noted above. However, the imaging array 12G in this alternative embodiment may have a series of one or more transceivers 18 positioned on an outer surface 65 of the imaging array 12G. An interconnection network as described elsewhere herein may be also embedded inside at least a portion of the carrier base 14G. Each transceiver 18 may be operatively associated with a corresponding interconnect 24 that is in communication with one or more conductive pathways within the interconnection network as described elsewhere herein. As shown, one or more terminal ends 44 can be defined along the carrier base 14G for operative association with a computer system during operation of the imaging array 12G.

Figure 6:
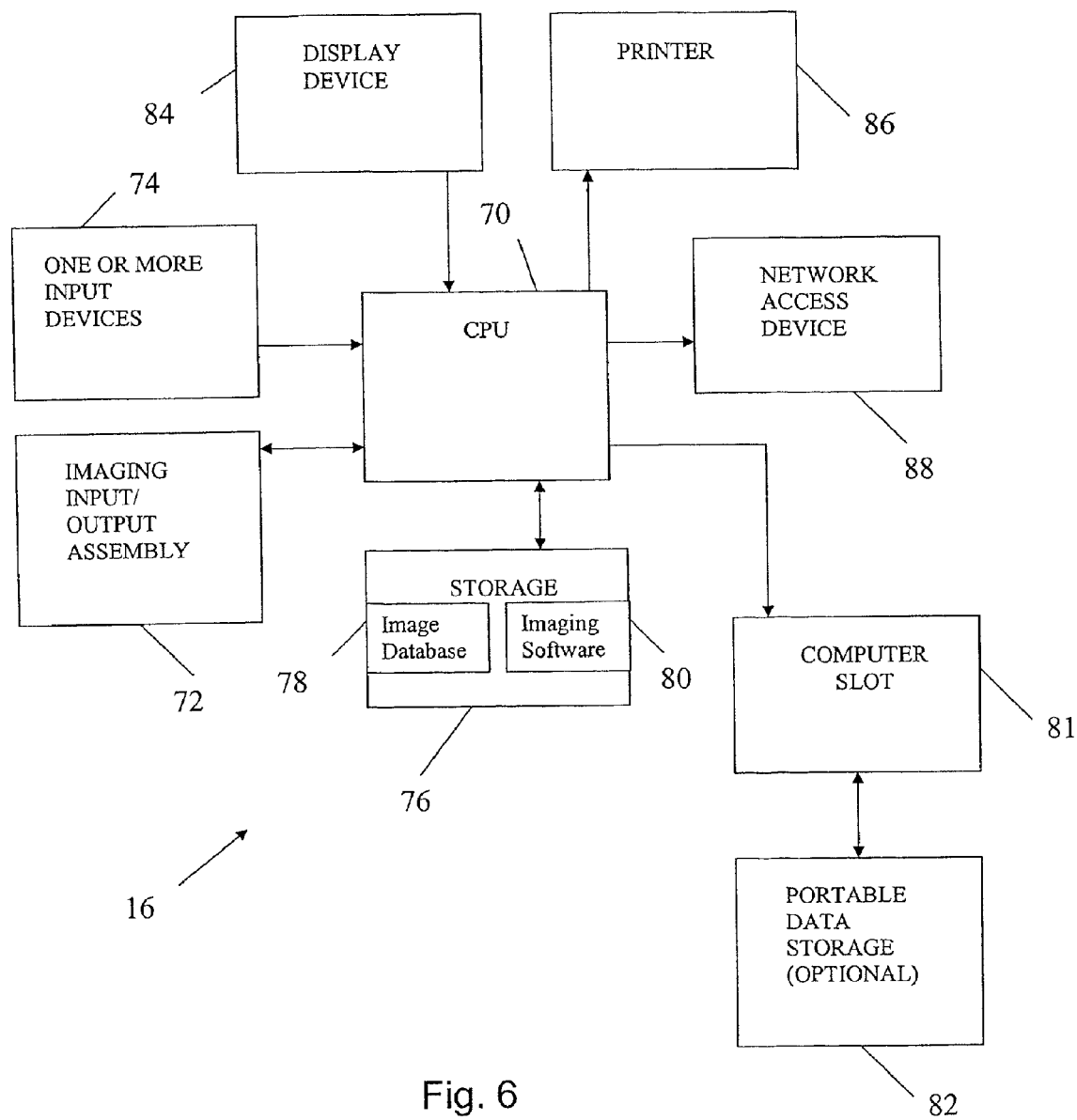
FIG. 6 is a simplified block diagram of a computer system.

FIG. 6 illustrates another aspect of the invention that provides an imaging computer system 16. The imaging computer system 16 includes a central processing unit (CPU) 70, and an imaging input/output assembly 72, one or more input devices 74, a memory storage 76 a computer slot 81, a display device 84, a printer 86 and a network access device 88, which can be each electrically connected or otherwise coupled to the CPU 70. Those skilled in the art will appreciate that computer system 16 may be implemented as a general-purpose computer or a specialized device (e.g. an ultrasound system) consisting of a combination of hardware and/or software. Other configurations of the computer system 16 are also contemplated herein. Furthermore, the CPU 70 may direct the operation of the various components of computer system 16. In one embodiment, the CPU may be a single central processing unit (CPU) operating at a speed of 3 gigahertz or greater that is housed within a motherboard (not shown), however other CPUs of differing speeds and configurations including multiple CPUs are also contemplated herein. Examples of CPUs that can be incorporated with this embodiment of the invention include Intel i960 and Motorola PowerPC processors, however other CPUs 70 may be also selected.

The imaging input/output assembly 72 may interface with an imaging array through a connection to send and receive data as provided by other aspects of the invention described elsewhere herein, e.g., FIG. 1. In a preferable embodiment, the imaging input/output assembly 72 may communicate with a Universal Serial Bus (USB) port. However other interfacing ports in association with applicable telecommunication protocols are also contemplated herein including a serial port, a parallel port, a "Firewire" protocol (IEEE 1394) port, and various wireless protocols. Furthermore, the input/output assembly may include a translator board in cooperation with a supporting software application. The translator board may include controlling electronics for a data acquisition pad as described herein, and may also have data processing capability for a large 2D/3D data set. Moreover, the translator board may work with any Windows, Apple, Unix or Sun Solaris platform. The translator board may process and transmit real-time or stored data between a silicon-based pad and existing front-end electronics through a USB connector or another standard system bus or an interface different than standard interfaces.

One or more input devices 74 may be electrically connected to the CPU 70 through a port (not shown) to receive input from a user of computer system 16. The user may operate the computer system 16 through the operation of one or more input devices 74, such as by providing commands through a keyboard and a mouse. It shall be understood that alternate peripheral and internal devices beyond a keyboard and a mouse as will be appreciated by those skilled in the art may be used to obtain direction from a user of computer system 16.

The memory storage 76 may be selected with capacity to hold and retain data in a digital form for access by CPU 70. The memory storage 76 may be separated into a primary storage and/or a secondary storage, and may include respective memory allotted for each. In one embodiment of the invention, the storage 76 can consist of a 250 gigabyte hard drive and 512 megabytes of RAM (random access memory). However other types of memory configurations and devices with differing access speeds and capacities are also contemplated herein. In addition, the memory storage 76 may also retain various software applications and database information. For example, an imaging software program 80 and an image database 78 may be selected and loaded into memory depending on selected applications. The image database 78 may be used with implementations where data is obtained from readings from an imaging array including those provided in accordance with other aspects of the invention described herein. The imaging data can be stored in the image database 78 for later use with the imaging software program 80 or other applications. In a preferable embodiment, the image database 78 is a SQL database but other implementations are also contemplated. A variety of imaging software programs 80 may be used for imaging, diagnostics and/or therapeutic delivery. Further description regarding the operation and components of the imaging software 80 are described in greater detail below. The imaging software 80 may access and manage data in the image database 78 which include tables and/or databases for the generated ultrasound data/image, comparison data, statistical processing, pattern recognition and/or diagnostic support. In another embodiment of the invention, the image database 78 may be stored in the memory storage 76, while in other embodiments the image database 78 may be stored in another memory device located onsite or at a remote location (not shown).

As shown in FIG. 6, other optional devices may be coupled to the CPU 70. The computer slot 81 may be selected to engage and receive information from an optional portable data storage 82. The portable data storage 82 may be used to retain the imaging history of a particular user or patient. In one embodiment, the portable data storage 82 is a flash memory card. Other embodiments of portable data storage 82 that are capable transferring, storing and transporting electronic data between one or more electronic storage devices are also contemplated. Furthermore, the display device 84 may be a selected device capable of visually presenting data to a user of computer system 16 or a patient. Examples of display devices 84 include personal computer (PC) screens, projection televisions, plasma televisions, liquid crystal displays (LCD), and digital light processing (DLP) displays. In addition, the printer 86 may be a selected device capable of making a print out or other hard copy of desired data. Examples of printers 86 include various impact and non-impact printers such as dot matrix printer, daisy wheel printer, chain and brand printer, ink jet printer, thermal transfer printer, bubble jet printer, page printer, LED/LCD printer, dye sublimation printers, digital photo printers, multifunction printer and laser jet printer. In an alternative embodiment of the invention, a network access device 88 may enable computer system 16 to contact outside resources (not shown) to send and store data. Outside resources may include computer or computer services on an intranet or an extranet (Internet). The network access device 88 may also include an internal or external network card, a modem, and other wired and wireless accesses devices as will be appreciated by those skilled in the art. In a preferable embodiment of the invention, the computer system 16 may be AN2300 Digital Ultrasound Engine offered by Analogic, but other computer systems are also contemplated. It shall be understood that the ultrasound imaging and other data acquisition apparatus and methods described herein can be applied to other computer systems or ultrasound systems used in the medical field and healthcare environment.

Figure 7:
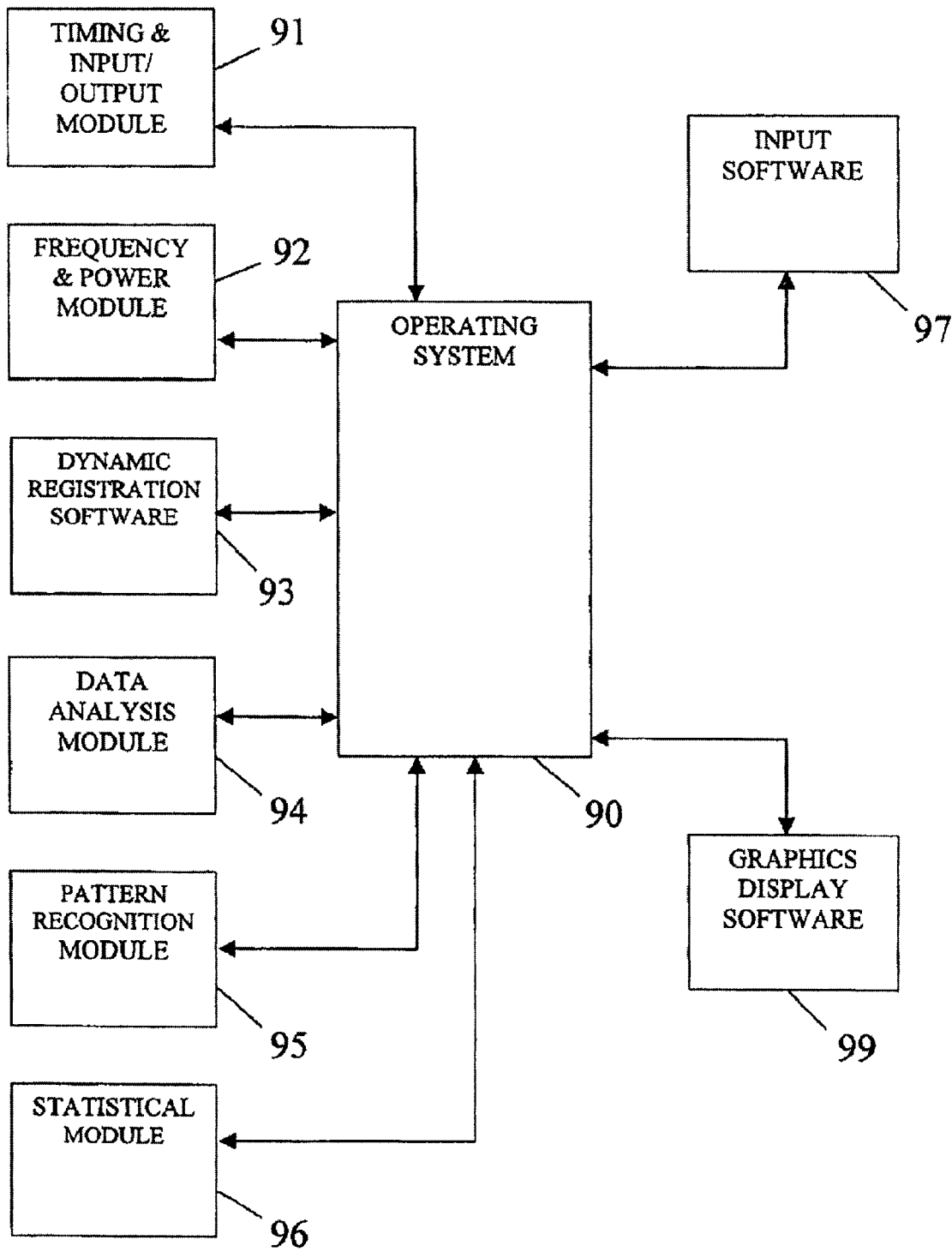
FIG. 7 is a simplified block diagram of imaging software for a computer system.

FIG. 7 illustrates an implementation of an imaging software program 80 that can be used in accordance with this aspect of the invention. In this embodiment, an operating system 90 may be in communication with an integrated circuit such an application specific IC (ASIC), field programmable logic device (FPLD) or field programmable gate array IC (FPGA), chip-set or processing circuit board and the imaging software 80 that includes various modules and software such as timing and input module 91, a frequency and power module 92, a dynamic registration software 93, a data analysis module 94, a pattern recognition module 95, a statistical module 96, as well as an input software program 97 and a graphics display software program 99. The operating system 90 may control the general operation of the computer system 16 including performing various system calls to control the computer system on a system level. In one embodiment of the invention, the operating system 90 may be Microsoft® Windows XP program, but other operating systems 90 such as Microsoft® Windows XP and ThreadX® Real-Time Operating System (RTOS) are also contemplated.

The imaging software program may include a variety of different modules. For example, the timing and input/output module 91 may be selected to initiate and truncate initiation signals with precise timing in communication with the frequency and power module 92 according to each transceiver 18 to which the initiation signals are directed. The frequency and power module 92 may be used to determine the requisite amount of power to provide transceivers 18 to generate appropriate frequencies for the analysis signals. Moreover, the dynamic registration module 93 may control the emission of initiation signals to establish the location of one transceiver 18 with regard to another transceiver and may continue to operate dynamically during the procedure to register changes in the relative positions as a result of patient movement and provide corrections if needed. The reverse operation may receive detection signals through receiving transceivers 18 in return through frequency and power module 92 from transmitting transceivers while recording the signal strength and timing.

Furthermore, the computer system 16 may capture the data from returning signals, compare the data to outgoing signal timing, power and other parameters and perform calculations to produce imaging information. In one embodiment of the invention, the imaging information may be translated to represent the structure shape and density of the tissue imaged. The imaging information may be also used to create a visual representation in 2D or 3D or a viewing monitor and or print out. A preferable embodiment of the invention, a diagnostic application is provided for ultrasound imaging used at both higher and lower frequencies at specific times to achieve image enhancement, three dimensional quality and real-time operation. Higher frequencies such as 5 to 10 MHz may provide a higher imaging quality with an improved axial resolution and lower frequencies such as 2 to 4 MHz may penetrate deeper body tissues. The use of a broad bandwidth of frequencies matched to the operation being performed may enable desired imaging resolutions.

The data analysis module 94 may use the output of the imaging data to create an image that can be viewed visually or in three-dimensional format or be directly translated into image data that can be directly interpreted by electronic or automated comparison to input software 97. The data analysis module 94 may use the output of the imaging data to determine whether a particular area is an area of concern. In one embodiment, the determination of whether a particular area is an area of concern may be by comparing current imaging data against previously stored imaging data, while in another embodiment the determination of whether a particular area is an area of concern is by comparing current imaging data against a general range for a type tissue.

The statistical module 96 may contain data from established medical guidelines and clinical evidence typically used by medical professionals to analyze images for comparison to established guidelines to make a determination of areas of concern.

The pattern recognition software 95 may contain patterns, data, and decision parameters that may be applied to the output of data analysis module 94 that presents the represented image or data from the current imaging procedure. The pattern recognition module (95) may support selection of or the identification of structures, dimensions, and anomalies through electronic comparison to the input software 97 containing the established normal data for the structures of interest. The data from the comparison may generate data for the differences and amount of variation between the input software 97 normal ranges and the current image data from the data analysis module 94 which may then be analyzed by the statistical module 96.

The input software 97 may contain data from established medical guidelines and clinical evidence that may be used by individuals in reading images for comparison to established guidelines to make the determination of normal. The data may include information such as tissue density, thickness, regularity, size, opaqueness and placement.

The graphics display software 99 may take information from the data analysis module 94, as may be adjusted by the dynamic registration software 93, and translate the information into a visual representation such as may be compatible with a graphics display screen. In one embodiment, the graphics display screen is a computer monitor, but other screens are also contemplated. In one embodiment, the visual representation is three dimensional and display in real-time, although other dimensional representations and timings are also contemplated. In one embodiment, the visual representation may be in color, although other non-color representations are also contemplated.

It shall be understood that various imaging software programs may be selected for use with invention herein. Computer systems may include different types of application software programs including ultrasound programs for specific applications and kinds of images that may be selected from a menu or downloaded as chosen by the user.

Figure 8:
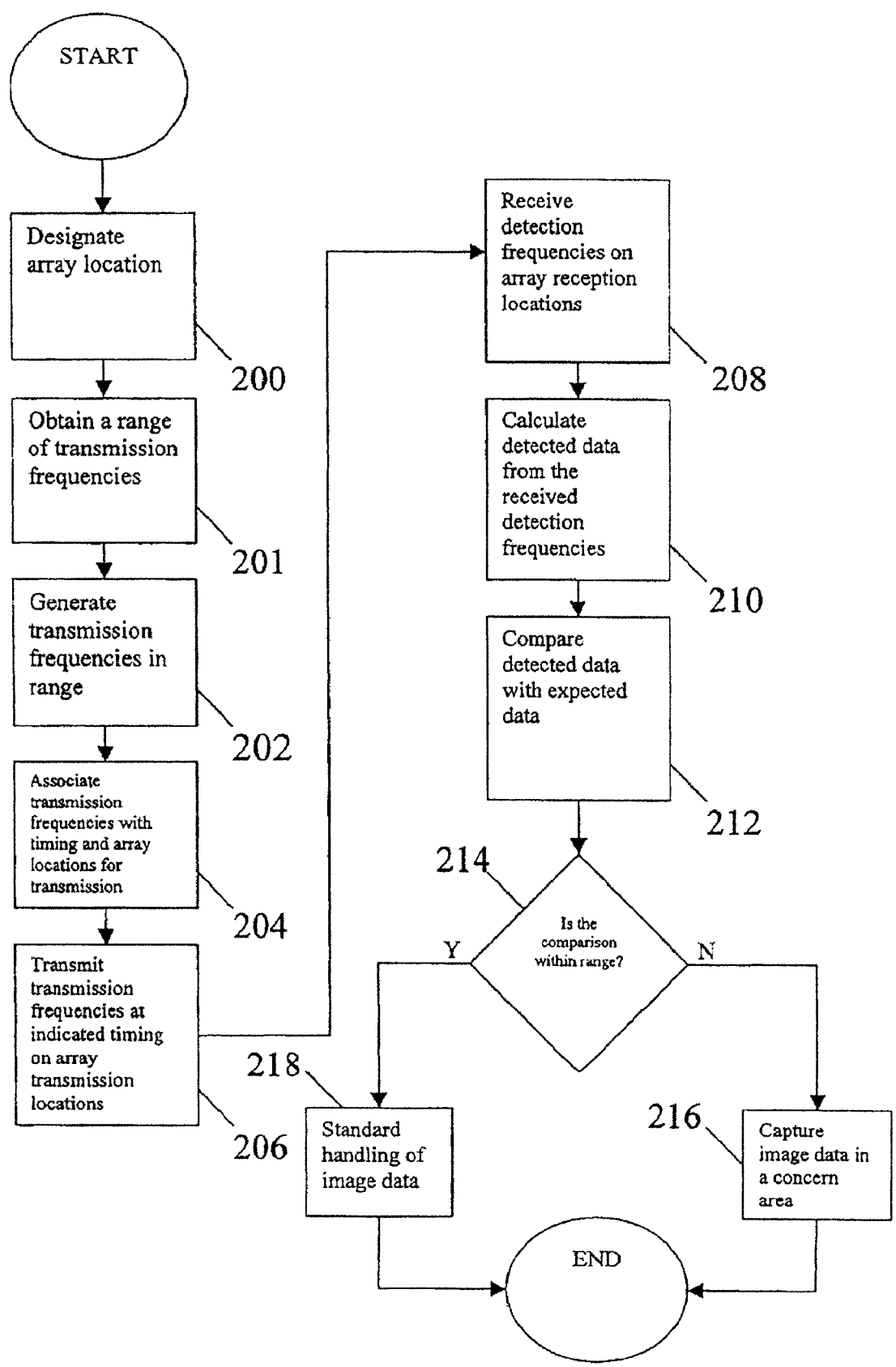
FIG. 8 is a flow chart illustrating operation of the imaging system.

Another aspect of the invention provides methods of performing imaging with the apparatus and systems provided herein. For example, FIG. 8 illustrates an implementation of an imaging operation that be performed which first includes a step 200 where one or more transceivers of an imaging array described elsewhere herein are designated in one or more array locations. In one embodiment of the invention for diagnostic applications, the transceivers may be discreetly organized into four different array locations. When selected transceivers are MEMS or cMUT types of devices, the number of elements may be selected as 64, 128, and/or 256, or more elements. However, different numbers of elements may be selected in other embodiments. The imaging operation next includes a step 201 where a computer system, e.g., FIG. 6 (16), obtains a range of transmission frequencies. In a preferable embodiment where the imaging array is being used for mammography, the range of frequencies may be 2-4 MHz, while in another embodiment where imaging array is being used for a deep body cavity read the range of frequencies may be 5-7 MHz. In an alternative embodiment, the range of frequencies can be based on prior clinical information as used during ultrasound readings. However other frequency ranges as will be appreciated in the art are also contemplated.

The computer system at step 202 then generates the transmission frequencies within the desired range. A broad bandwidth of frequencies can be used, however other usage of frequencies are also contemplated. An analysis signal may be intermittently pulsed to reduce the heating of tissue, or may be continuous to provide ultrasound therapy to treat injured muscles and tissues. In an embodiment where the imaging system may be used for diagnostic applications, a broad bandwidth of frequencies may be selected and generated which include higher frequencies such as 5-10 MHz to provide relatively better imaging quality with a better axial resolution and lower frequencies such as 2-4 MHz to penetrate deeper body tissues.

The computer system at step 204 can next associate the transmission frequencies with selected timing and array locations for transmission and reception. The analysis signals can be directed towards different locations of the imaging array. It should be appreciated that the imaging systems selected herein may designate array locations to control the pulse generation and pulse transmission timing and reduce the listening time for receiving returning echoes. In one embodiment of the invention, an array location may be used for both sending analysis signals and receiving detection signals, while in another embodiment different array locations may be used for sending analysis signals and receiving detection signals. Alternatively, the analysis signals and detection signals may be sent and received nearly simultaneously.

The computer system at step 206 can next initiate the transmission of the analysis signals at selected frequencies at the indicated timing on array transmission locations. The array transmission locations may be where one or more transceivers that have been designated by the computer system for transmission.

Thereafter at step 208, the computer system can receive the detection signals on array reception locations. The array reception locations may be one or more transceivers that have been designated by the computer system for reception.

The computer system at step 210 then calculates the imaging data from the received detection signals at step 210. Thereafter, the computer system at step 212 may compare imaging data against expected data.

At decision point 214, the computer system can determines if the comparison (i.e., the imaging data against the expected data) is within a selected or desired range. If the imaging data is within range, then computer system at step 218 may handle the imaging data in a standard or predetermined way. In one embodiment, the handling the imaging data in a standard way may be to store the imaging data in an image database. If the imaging data is not within range, the computer system at step 216 may proceed to capturing the imaging data for the area of concern. After step 216 or step 218 is performed, this implementation of creating images in accordance with this aspect of the invention is complete (END).

Figure 9:
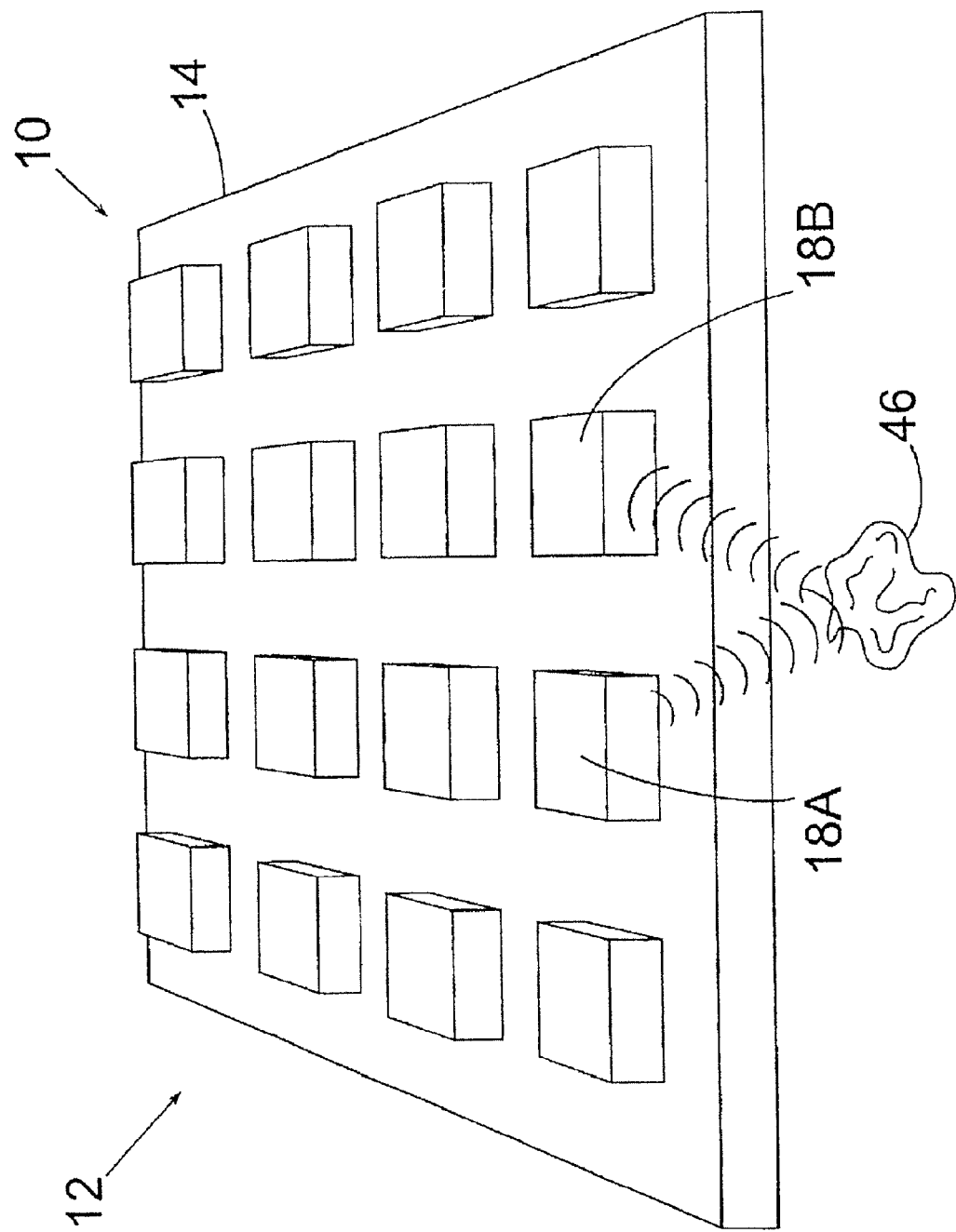
FIG. 9 is a simplified perspective view of an imaging array illustrating the detection of an object.

FIG. 9 describes another aspect of the invention that provides imaging systems and methods with groups of transceivers that can selectively transmit and receive imaging signals. A plurality of transceivers within an imaging array such as those described elsewhere herein may each have the capability of transmitting analysis signals and receiving detection signals. By way of example, a transceiver 18A may transmit one or more analysis signals that are deflected by an object 46 and received by a transceiver 18B in order to provide information to a computer system in order to produce an image based on such the imaging data. As such, transmission of one or more analysis signals sent by one or more transceivers 18A may be received by those particular transceivers 18B or any of the other transceivers as desired. In a preferable embodiment of the invention, one or more transceivers may be grouped into array locations such that transceivers 18A at one or more locations send a detection analysis signal, and one or more transceivers 18B at one or more locations may receive a detection signal.

Figure 10A:
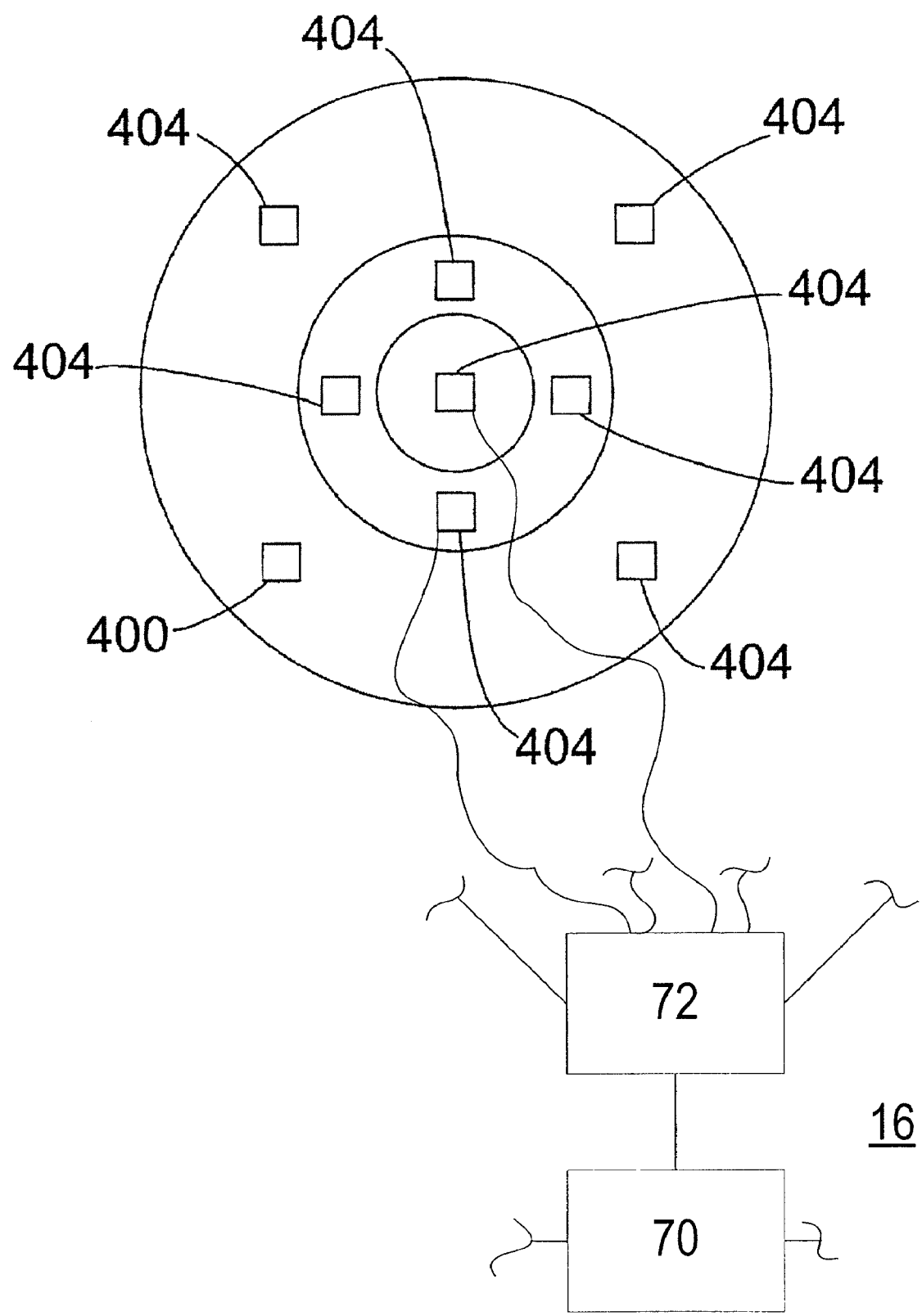
FIG. 10A is a simplified cross-sectional view of an embodiment of a concentric circles scanning pattern.

Another aspect of the invention provides systems and methods for performing imaging scans according to a predetermined pattern with configurable transceivers. Referring to FIG. 10A, an implementation of following a concentric circles scanning pattern is illustrated. In this implementation, a transceiver 400 may be designated as both a transmitting transceiver and a receiving transceiver. Meanwhile, other transmitting transceivers may send an analysis signal and receiving transceivers may receive a detection signal. Unused transceivers 404 may neither transmit nor receive signals during this scanning pattern. It shall be understood that this and other embodiments of the invention below may be applied to transceivers illustrated in this and other figures herein such that any group of one or more elements can be configured and controlled by computer to selectively transmit and/or receive analysis signals (see FIG. 6).

Figure 10B:
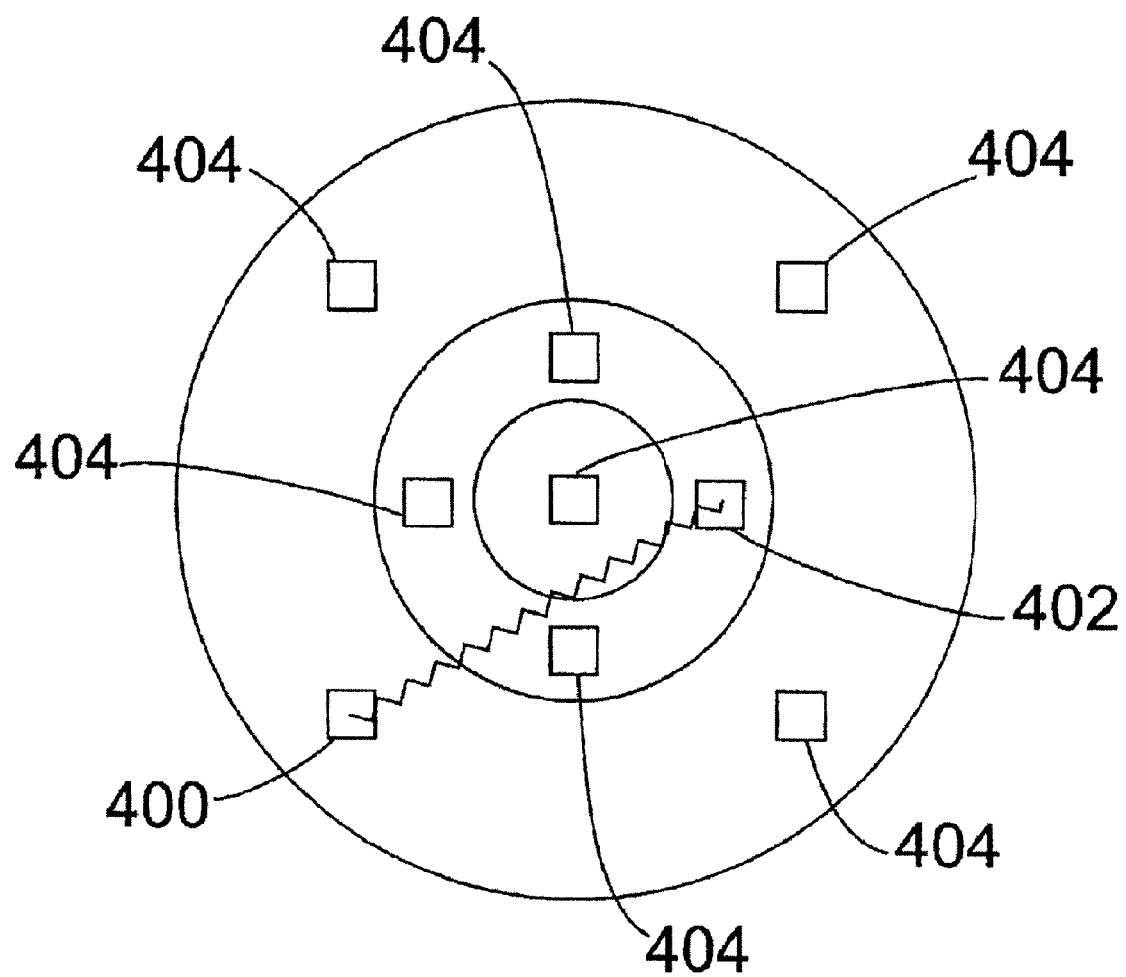
FIG. 10B is a simplified cross-sectional view of an embodiment of a concentric circles scanning pattern.

Referring to FIG. 10B, an implementation using a concentric circles scanning pattern is illustrated. In this implementation, a first transceiver may be designated as transmitting transceiver 400 and a second transceiver may be designated as receiving transceiver 402. The transmitting transceiver 400 may send an analysis signal (shown with staggered lines herein) and the receiving transceiver 402 may receive a detection signal. Unused transceivers 404 may neither transmit nor receive signals during this scanning pattern.

Figure 10C:
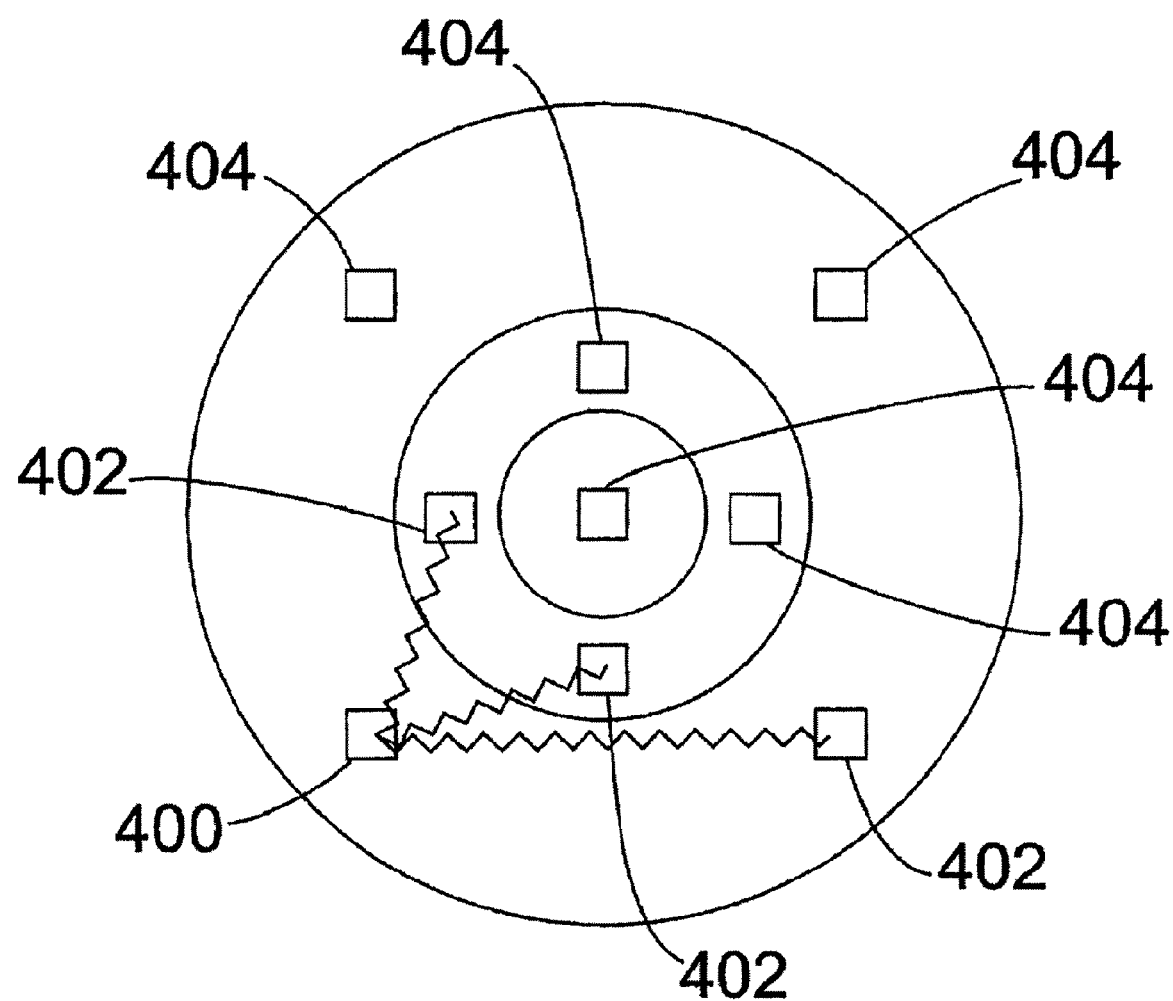
FIG. 10C is a simplified cross-sectional view of an embodiment of a concentric circles scanning pattern.

Referring to FIG. 10C, another implementation using a concentric circles scanning pattern is illustrated. In this implementation, a first transceiver may be designated as transmitting transceiver 400 and three transceivers may be designated as receiving transceivers 402. The transmitting transceiver 400 may send an analysis signal and each receiving transceiver 402 may receive a detection signal. Unused transceivers 404 may neither transmit nor receive signals during this scanning pattern. Again it shall be understood that any number of transceivers shown in this and other figures herein can configured to transmit and/or receive analysis signals or no signal at all.

Figure 10D:
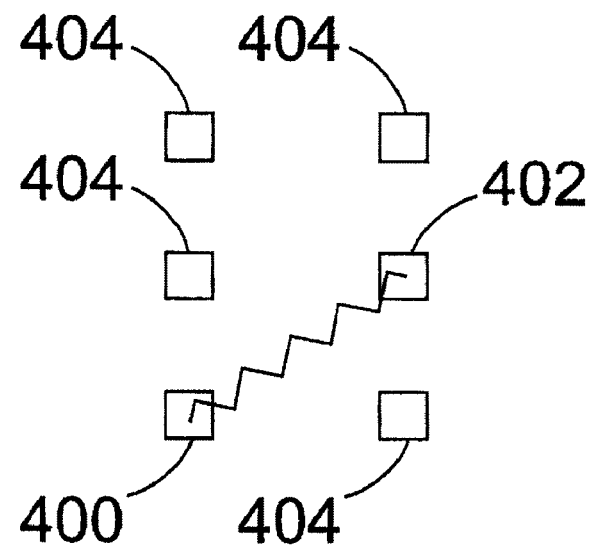
FIG. 10D is a simplified cross-sectional view of an embodiment of a line-to-line scanning pattern.

Other patterns besides concentric circle scanning patterns can be alternatively used also. Referring to FIG. 10D, another embodiment of the invention providing a line-to-line scanning pattern is illustrated. In this implementation, a first transceiver may be designated as transmitting transceiver 400 and a second transceiver may be designated as receiving transceiver 402. The transmitting transceiver 400 may send an analysis signal and the receiving transceiver 402 may receive a detection signal. Unused transceivers 404 may neither transmit nor receive signals during this scanning pattern. This and other line-to-line scanning implementations herein can be applied to any of the concentric circles transceiver patterns described above or vice versa.

Figure 10E:
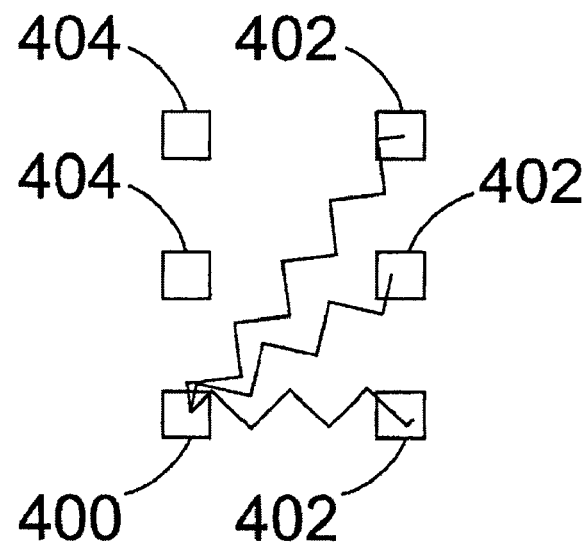
FIG. 10E is a simplified cross-sectional view of an embodiment of a line-to-line scanning pattern.

Referring to FIG. 10E, another implementation of a line-to-line scanning pattern is illustrated. In this implementation, a first transceiver may be designated as transmitting transceiver 400 and a group of three transceivers may be designated as receiving transceivers 402. The transmitting transceiver 400 may send an analysis signal and each receiving transceiver 402 may receive a detection signal. Unused transceivers 404 may neither transmit nor receive signals during this scanning pattern.

Figure 10F:
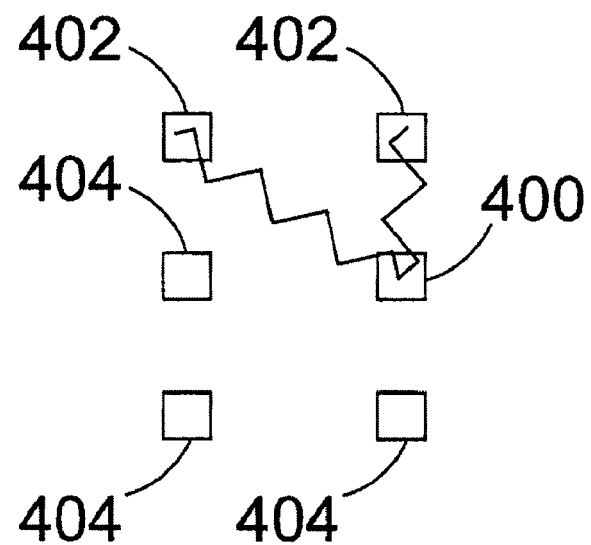
FIG. 10F is a simplified cross-sectional view of an embodiment of a line-to-line scanning pattern.

Referring to FIG. 10F, yet another implementation of a line-to-line scanning pattern is illustrated. In this implementation, a first transceiver may be designated as transmitting transceiver 400 and two transceivers may be designated as receiving transceivers 402. The transmitting transceiver 400 may send an analysis signal and each receiving transceiver 402 may receive a detection signal. Unused transceivers 404 may neither transmit nor receive signals during this scanning pattern.

Figure 10G:
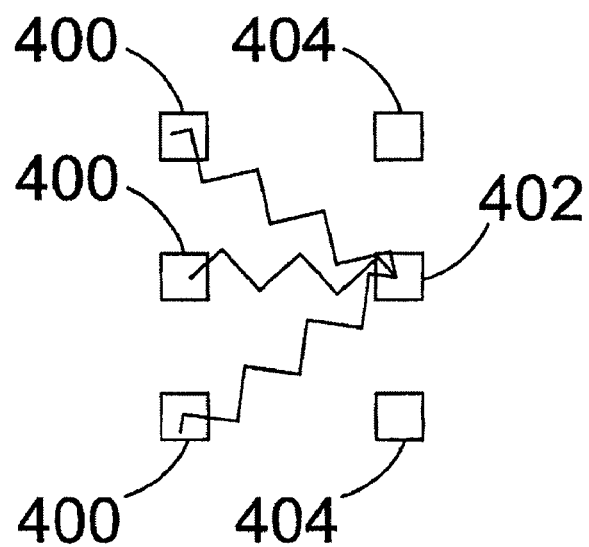
FIG. 10G is a simplified cross-sectional view of an embodiment of a line-to-line scanning pattern.

Referring to FIG. 10G, another alternative implementation of a line-to-line scanning pattern is illustrated. In this implementation, a group of three transceivers may be designated as transmitting transceivers 400 and a transceiver may be designated as a receiving transceiver 402. The transmitting transceivers 400 may each send an analysis signal and the receiving transceiver 402 may receive a detection signal. Unused transceivers 404 may neither transmit nor receive signals during this scanning pattern.

Figure 10H:
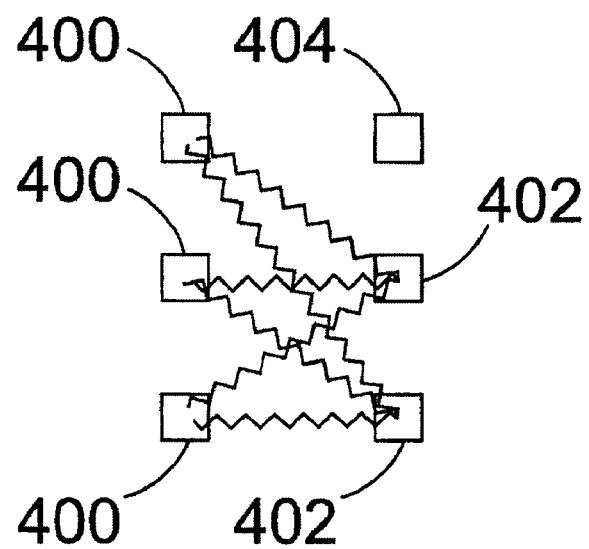
FIG. 10H is a simplified cross-sectional view of an embodiment of a line-to-line scanning pattern.

Referring to FIG. 10H, yet another alternative implementation of a line-to-line scanning pattern is illustrated. In this implementation, a group of three transceivers may be designated as transmitting transceivers 400 and two transceivers may be designated as receiving transceivers 402. Each transmitting transceivers 400 may send analysis signals and each receiving transceiver 402 may receive detection signals. The unused transceiver 404 may neither transmit nor receive signals during this scanning pattern.

Figure 10I:
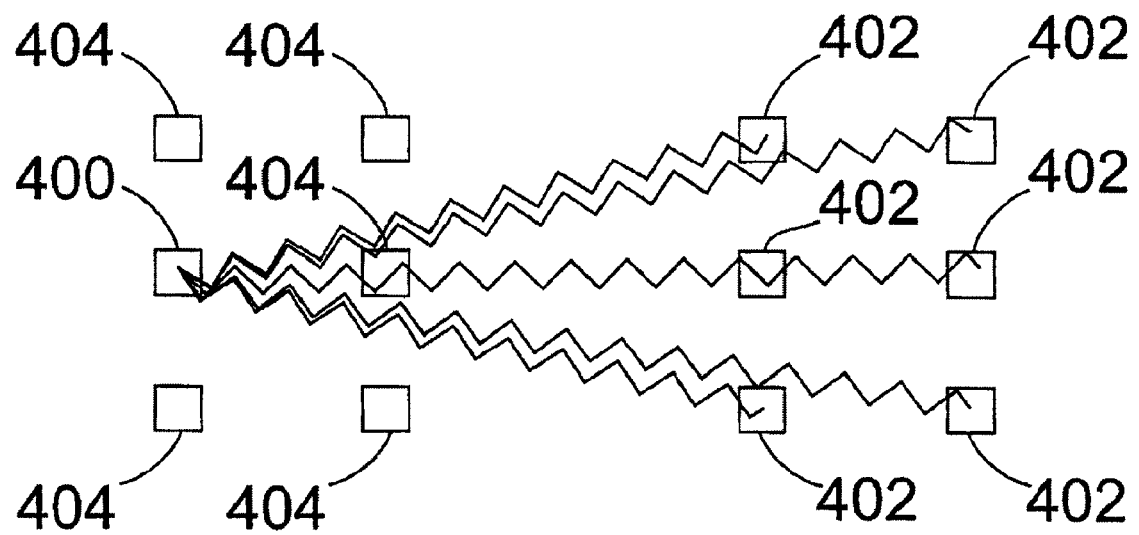
FIG. 10I is a simplified cross-sectional view of an embodiment of a group-to-point scanning pattern.

Referring to FIG. 10I, another embodiment of the invention providing a group-to-point scanning pattern is illustrated. In this implementation, a group of six transceivers may be designated as transmitting transceivers 402 and a transceiver may be designated as receiving transceiver 400. Each transmitting transceiver 402 may send an analysis signal, and the receiving transceiver 400 may receive the detection signals. Unused transceivers 404 may neither transmit nor receive signals during this scanning pattern.

Figure 10J:
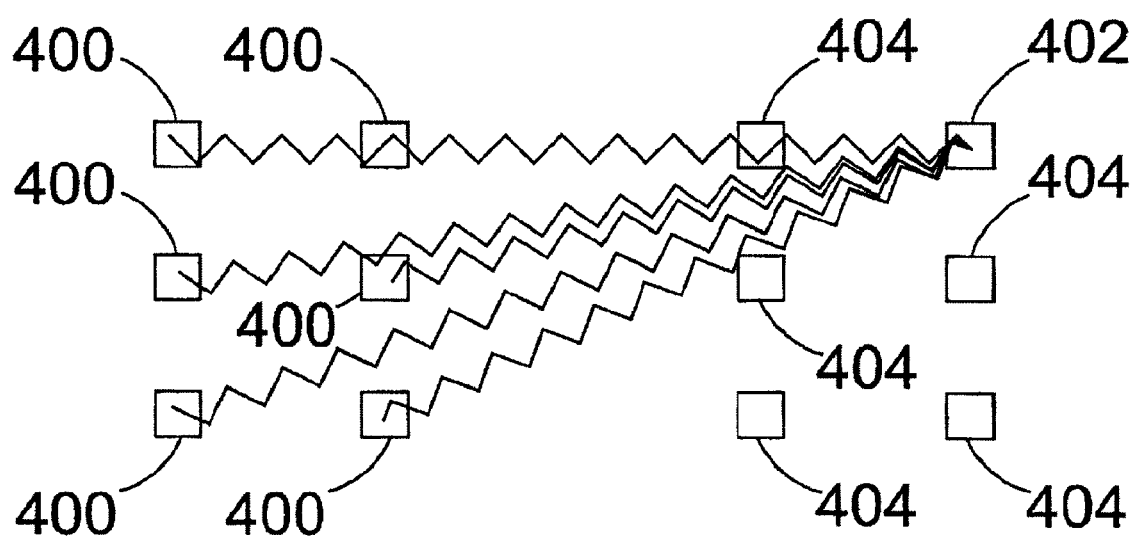
FIG. 10J is a simplified cross-sectional view of an embodiment of a point-to-group scanning pattern.

Referring to FIG. 10J, another embodiment of the invention providing a point-to-group scanning pattern is illustrated. In this implementation, a transceiver may be designated as a transmitting transceiver 402 and a group of transceivers may be designated as receiving transceivers 400. The transmitting transceiver 402 may send analysis signals and each receiving transceiver 400 may each receive a detection signal. Unused transceivers 404 may neither transmit nor receive signals during this scanning pattern.

Figure 11:
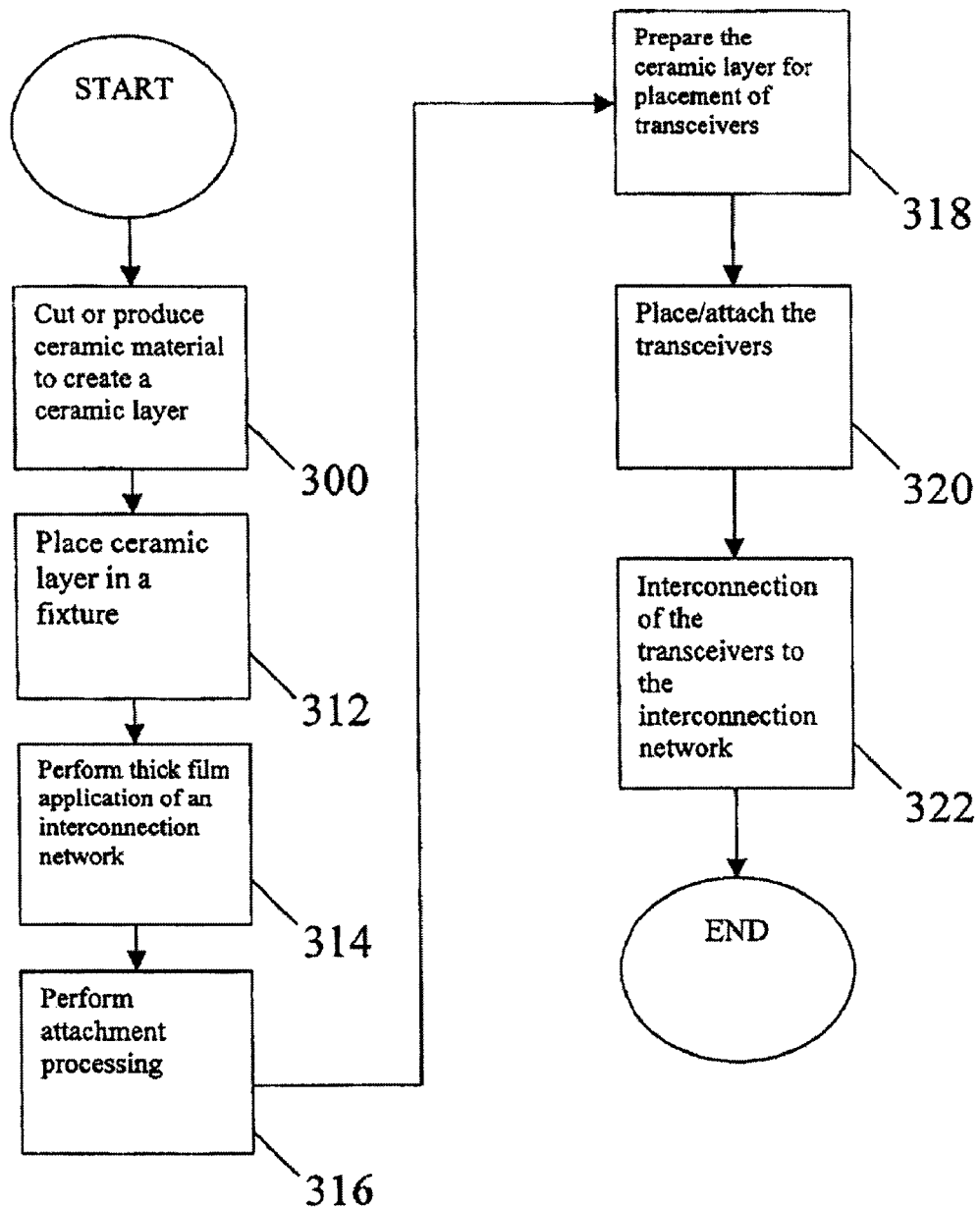
FIG. 11 is a flow chart illustrating a method for manufacturing an embodiment of an imaging system having a ceramic carrier base.

FIG. 11 illustrates yet another aspect of the invention that provides methods for manufacturing configurable imaging arrays provided in accordance with other aspects of the invention, e.g., FIG. 3A (12A). In this implementation, a user at step 300 produces and then cuts to a predetermined configuration a ceramic material for providing a ceramic layer as described elsewhere herein, e.g., FIG. 3C (53). The user may then place the ceramic layer in a fixture (not shown) at step 312. Once the ceramic layer is in the fixture, at step 314 a thick film application can be performed to produce a conductive pathway and interconnects on the outer surface area of the ceramic layer forming the carrier base in order to produce the interconnection network, e.g., FIG. 5A. At step 316, an attachment process can be also performed. In an alternative embodiment of the invention, the attachment process may follow the principles of low temperature co-firing ceramic technology using "green-stage" ceramic that has been dried and partially cured or fired, then aligned and subjected to additional temperature to bond the layers through an additional curing reaction process. After the attachment process 316, the ceramic layer may be prepared at step 318 for accepting placement of one or more transceivers. The ceramic layer 53 may be prepared by using screen printing, sputtering or evaporation deposition. A series of attachment pads, which act as "landing sites" for transceivers, can be also prepared for electrical and mechanical attachment by placing a conductive epoxy, metal preform or eutectic solder upon which a transceiver is placed. In a preferable embodiment, the attachment pads may be formed of conductive metals and materials such as silver, gold, epoxy and carbon. The one or more transceivers can be then positioned in a predetermined arrangement on the surface area of the ceramic layer at step 320 such that the interconnection network may then be operatively engaged or otherwise in communication with each transceiver.

The aforementioned attachment processes, e.g., step 316, may be performed in a variety of ways which include either a drying and curing process using heat and timing, or melting of the metal just before placing the transceivers, or use of ultrasonic power to form the bond between metallized material and the transceivers. Examples of preferable metal materials include: DuPont CB220 (copper) and CB230 (silver/copper) materials that are fully screenable and solderable and may be used on a wide variety of substrates to create fully additive circuits and crossovers; and DuPont 951 Green Tape™ system which may deliver line spacing and resolution as fine as 100 μm, via diameters as small as 100 μm, and can be fabricated with more than 100 layers. An example of a device manufactured according to this process yielded a produced circuit that had eight layers, nine conductive layers (including ground plane), 10-mil lines and spaces, and an average of 150 vias per layer. Another example device produced by such methods provided a circuit that was manufactured as part of a 12-up array using DuPont 951 Tape, 5734 metal-filled paste for the conductors, and 5718 Gold-loaded conductive paste for the via fill. The 943 Low Loss Green Tape™ system may deliver high frequency performance with minimal dielectric loss. In a preferable embodiment of the invention, the operative engagement may be accomplished by wire bonding, tape automated bonding (TAB), tape ball grid array (TBGA), flip chip bonding, through-wafer bonding, and evaporation and diffusion processing, however other methods used in the assembly of integrated circuits and MEMs devices which are also contemplated.

Figure 12:
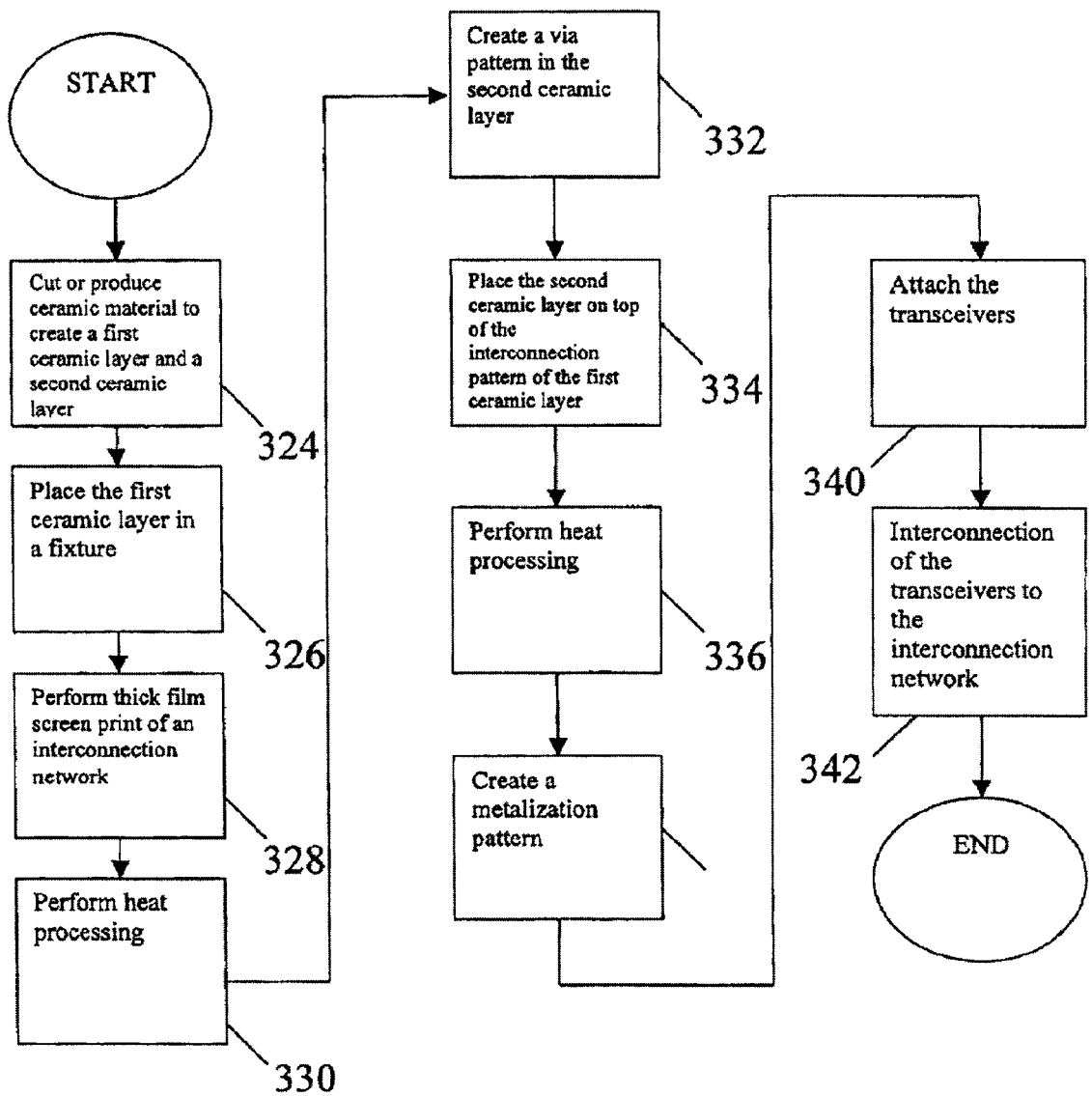
FIG. 12 is a flow chart illustrating a method for manufacturing another embodiment of an imaging system having a ceramic carrier base.

Referring to FIG. 12, another implementation of the invention is illustrated that provides a method for manufacturing a multi-layer imaging array, e.g., FIG. 3C. In this implementation, a first ceramic layer (48) and a second ceramic layer (49) at step 324 are provided and made from a flexible ceramic material known in the art and described elsewhere herein. The first ceramic layer may then be placed in a fixture (not shown) at step 326 for the securing ceramic layer for proper orientation and registration when applying an interconnection network. Once the first ceramic fabric layer is placed in the fixture, at step 328, a thick film screen print application may be utilized for applying a conductive paste, such as a paste made from titanium or other suitable metals and alloys suitable for electrical conductivity. At step 330, the first ceramic layer can be subjected to a heating process to dry and cure the conductive paste. At step 332, a pattern of holes may be formed through the second ceramic layer in a predefined pattern in order to construct each corresponding interconnect within the interconnection network. Once the pattern of holes are formed, the first ceramic layer at step 334 may be placed under and aligned with the second ceramic layer such that the holes are properly registered with certain portions of the conductive pathway and the holes are filled with a conductive paste as well as selected portions of the surface of the second ceramic layer. At step 336, a second heating process may be performed on the first and second ceramic layers such that the conductive paste is cured and the interconnects thereby constructed. After construction, a selected end of the interconnects may connect to the network, and the other end may include a metal attachment pad and a bonding pad for physical and electrical connection to a corresponding transceiver at step 340. After attachment of each transceiver to a respective the interconnect, at step 342, the transceivers can be operatively associated or otherwise connected with the interconnection network.

Figure 13:
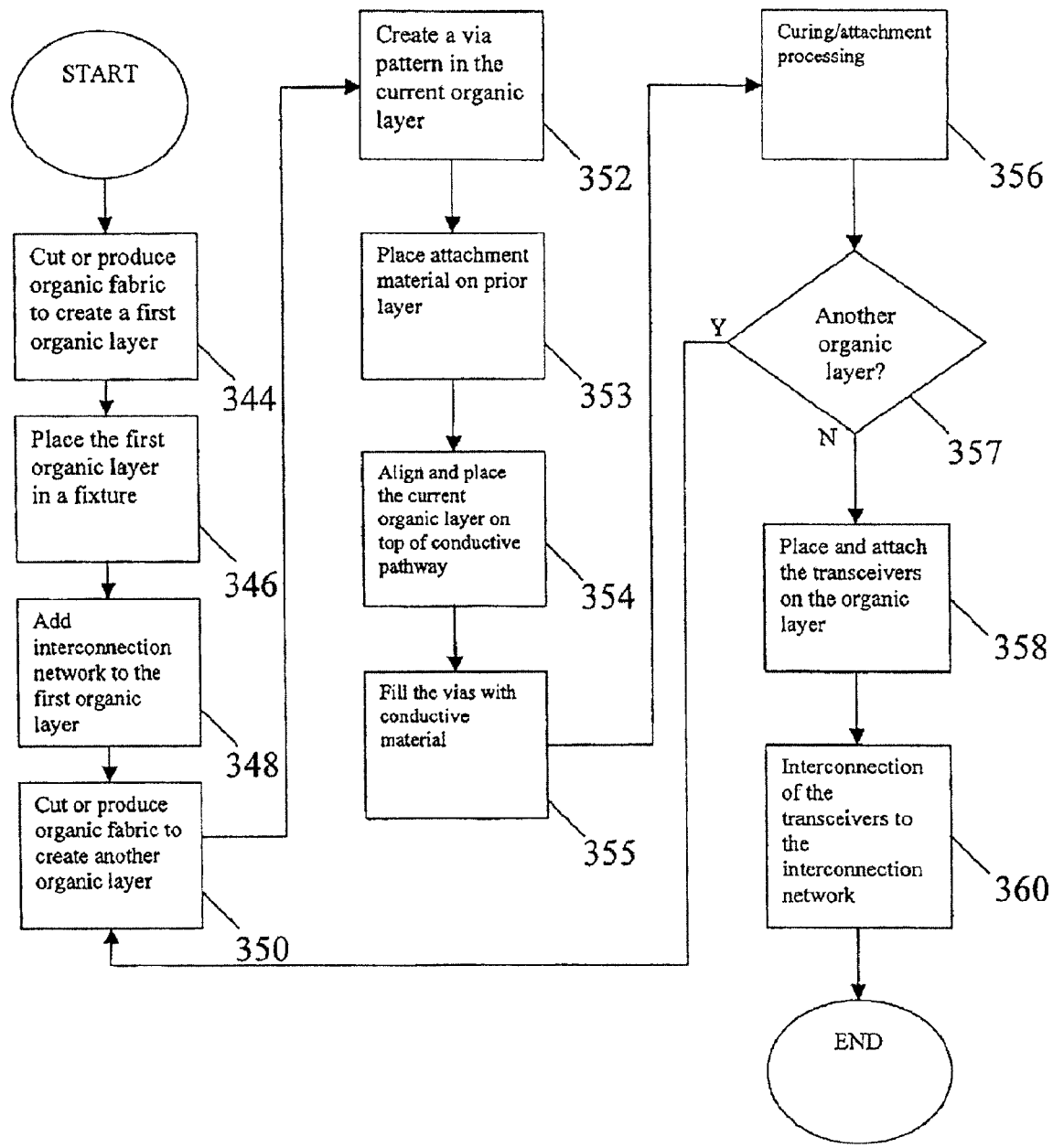
FIG. 13 is a flow chart illustrating a method for manufacturing an embodiment of an imaging system having an organic carrier base.

FIG. 13 illustrates yet another method for manufacturing an imaging array, e.g., FIG. 4A, in accordance with the invention. In this implementation, a first organic layer (54) made from an organic material can be cut or produced at step 344. At step 346, the first organic layer may be secured in a fixture (not shown). An interconnection network as described elsewhere herein may then be constructed on or added to the surface of the first organic layer using conductive paste or metallic pathways or a membrane circuit with conductive traces to form a conductive pathway (25) at step 348. In a preferable embodiment, the conductive pathway may be made by adding either metal wire, conductive paste or a membrane onto the first organic layer. The conductive pathway may be also formed with a pattern of metal wires or traces or conductive paste that allows the transmission of electrical current from an outside controlling source of imaging system, e.g., FIG. 1 (10), through a carrier base to a group of one or more transceivers. The structure and insulation of the conductive pathway may allow controlled access and timing for input and output detection signals. Another or a second organic layer (shown as a second organic layer 56) may be cut or produced at step 350. Once the first and the second organic layers are drawn or produced, corresponding vias (42) can be created through the second organic layer at step 352. In a preferable embodiment, the vias can be added in a regular or desired pattern, with the locations of the vias determined by the electrical signal sequencing predetermined for the signal control related to the procedure to be performed. At step 353 a desired attachment material may be placed on second organic layer 56. Thereafter, the second organic layer may be aligned and placed on top of the conductive pathway at step 354. In a preferable embodiment of the invention, the organic layers can be attached using an adhesive layer, application of heat or mechanical crimping or punch-through, or a combination of these and other techniques known to those skilled in the art. For example, with the use of an adhesive, either a layer or point application may apply an epoxy-type of liquid or semi-liquid material to the first organic layer. The second organic layer may be aligned, and the two layers brought together afterwards, followed by a drying and curing process step to achieve adhesive bonding. These steps may be repeated again for additional layers of organic materials depending upon a selected design and application of the final product. Heat at the melting point temperature may also be applied at selected locations to achieve a controlled re-melting and bonding of the layers following the alignment of the two or more layers. In an alternative embodiment, to mechanically attach the layers, post-alignment, it may be possible to use a punch-through or crimping operation accomplished with a laser, crimp or needle-like apparatus.

At step 355, a conductive material may be deposited inside vias for constructing each interconnect. Once the interconnects are constructed, the second organic layer may be placed over and aligned with the first organic layer at step 354 such that respective holes are properly registered with certain portions of the conductive pathway. The curing/attachment process may be performed next at step 356. With use of an adhesive, either a layer or point application may apply an epoxy-type of liquid or semi-liquid material to the first organic layer. The second organic layer may be aligned and the two layers brought together, followed by a drying and curing process step to achieve adhesive bonding. These steps may be repeated again for additional layers of organic materials dependent upon a selected design and application of the final product. Heat at the melting point temperature may also be applied at selected locations to achieve a controlled re-melting and bonding of the layers following the alignment of the two or more layers. In an alternative embodiment, to mechanically attach the layers, post-alignment, it may be possible to use a punch-through or crimping operation accomplished with a laser, crimp or needle-like apparatus. At decision point 357, if another organic layer is to be added, the method returns to step 350 and repeats steps 352-356 for the addition of another organic layer. If another organic layer is not be added, the method proceeds to step 358. The transceivers for the array are attached on the top most organic layer (e.g., second organic layer 54) at step 358. Thereafter, at step 360 the transceivers may be placed directly on top of and connected to a chip that controls various parameters such as timing, power or frequency and are interconnected to the interconnection network. This implementation of the forgoing array manufacturing method is thereafter complete.

Figure 14:
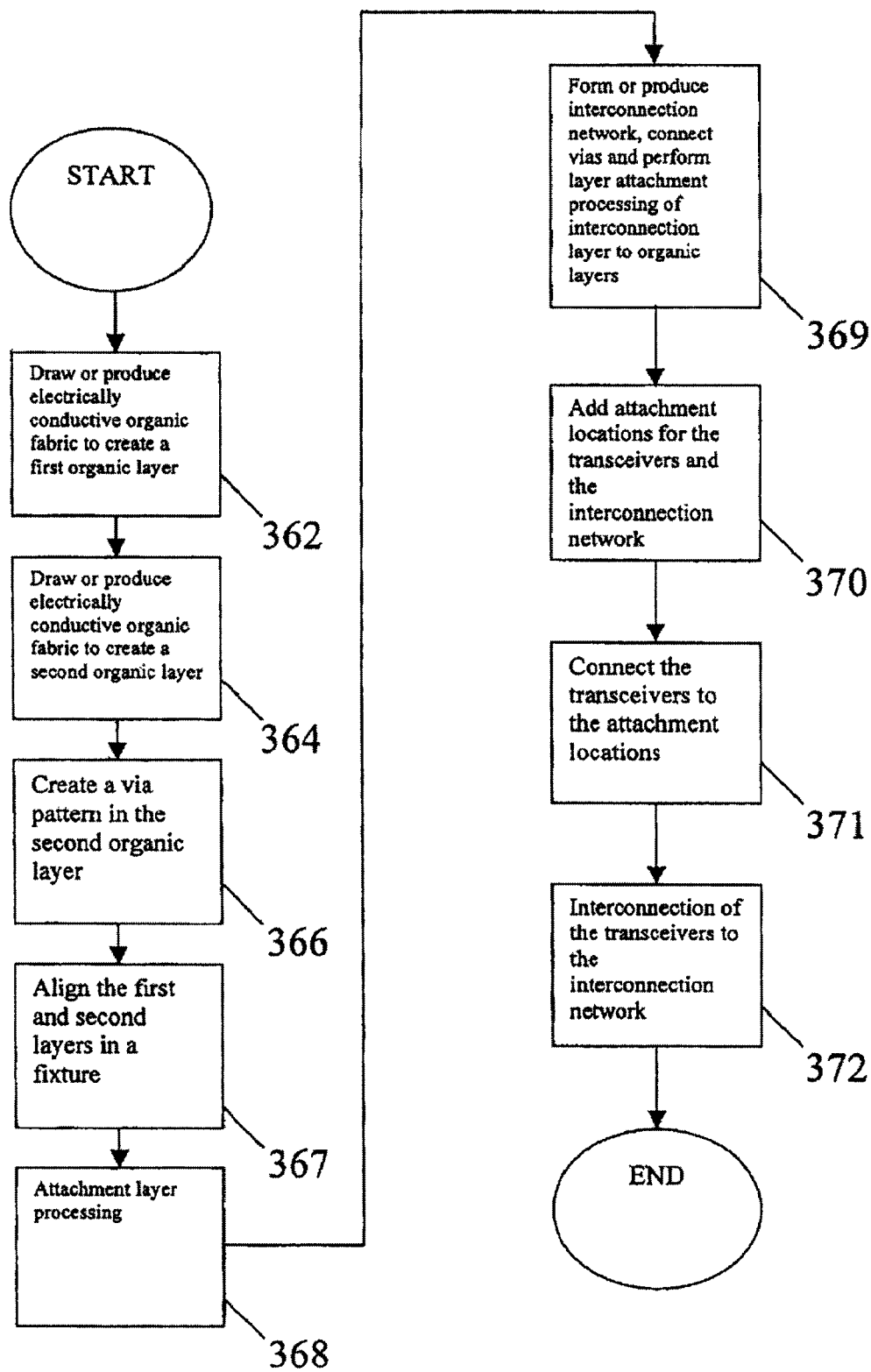
FIG. 14 is a flow chart illustrating a method for manufacturing another embodiment of an imaging system having an organic carrier base.

FIG. 14 illustrates yet another method for manufacturing an imaging array, e.g., FIG. 4B, in accordance with the invention that includes at least two organic layers, e.g., first organic layer 54 and second organic layer 56. In this implementation, an imaging array (12D) is manufactured having a first organic layer that can be made from an electrically conductive organic fabric that is drawn or produced at step 362. The first organic layer can be solid, but other states of the first organic layer are also contemplated, e.g., semi-solid, gel like. A second organic layer can also be selected and made from a variety of electrically conductive organic fabric which may be drawn or produced at step 364. The second organic layer may be added from molten filaments formed and placed on top of the electrical interlayer connection and the first organic layer. In one embodiment of the invention, a continuous-feed type of manufacturing operation may be used.

Once the first and the second organic layers are drawn or produced, a selected number of vias (42) can be created through the second organic layer at step 366. In one alternative embodiment, the vias can be added in a regular pattern, which may be determined by the electrical signal sequencing predetermined for the signal control related to the procedure to be performed. At step 367, the first organic layer may be aligned with the second organic layer in a fixture (not shown). Once the first and second organic layers are aligned in the fixture, the next step of attachment layer processing may be performed on the first organic layer and the second organic layer at step 368. Thereafter, at step 369 an interconnection network (20) may be formed or produced, the vias may be connected, and the interconnection network may be added by attachment layer processing as described elsewhere herein. In a preferable embodiment, the interconnection network may be a conductivity pathway placed between the first and the second organic layers to allow electrical signals to flow. The electrical interlayer connection may be achieved by adding either metal traces or wires, conductive paste or a membrane with conductive pathways, although others are also contemplated. In an alternate embodiment of the invention formed with both first and second organic layers, the electrical interlayer connection may be added on top of the first layer organic layer, while in another embodiment with more than two organic layers the electrical interlayer connection may be added on all but the last formed layer. When a desired number of input-output signals are selected, the imaging array may utilize additional electrical interlayer connections between additional organic layers to send and receive the signals with adequate separation and insulation of the conductive pathways to achieve a desired resistance, impedance, speed and reliability. The layer attachment processing step may be accomplished by layer bonding, application of an adhesive layer or heat, or mechanical crimping or punch-through, or a combination of these and other known techniques. In another alternate embodiment, he layer bonding may be achieved by applying heat, having a change of physical state, drying and curing to create a bond or attachment between the layers of organic fabric, following the step where the conductive core filaments are created, drawn, or formed and laid down in a fabric-like weave or pattern.

At step 370, a series of attachment locations can be added for the transceivers and the interconnection network. Thereafter, at step 371 each transceiver may be connected to corresponding attachment locations. In one embodiment, the connection may be both the physical attachment to the landing pad sites and the electrical connection to the interconnection network. After the connection process is completed, each transceiver can be operatively associated with the interconnection network at step 372. After step 372, an optional additional step may be followed in covering the transceivers with a gel-like material such as those described elsewhere herein, e.g., FIG. 5A. It should be appreciated that the number of organic layers used in this and other particular embodiments described herein may depend on the desired electrical signal complexity for a particular application and imaging array.

Figure 15:
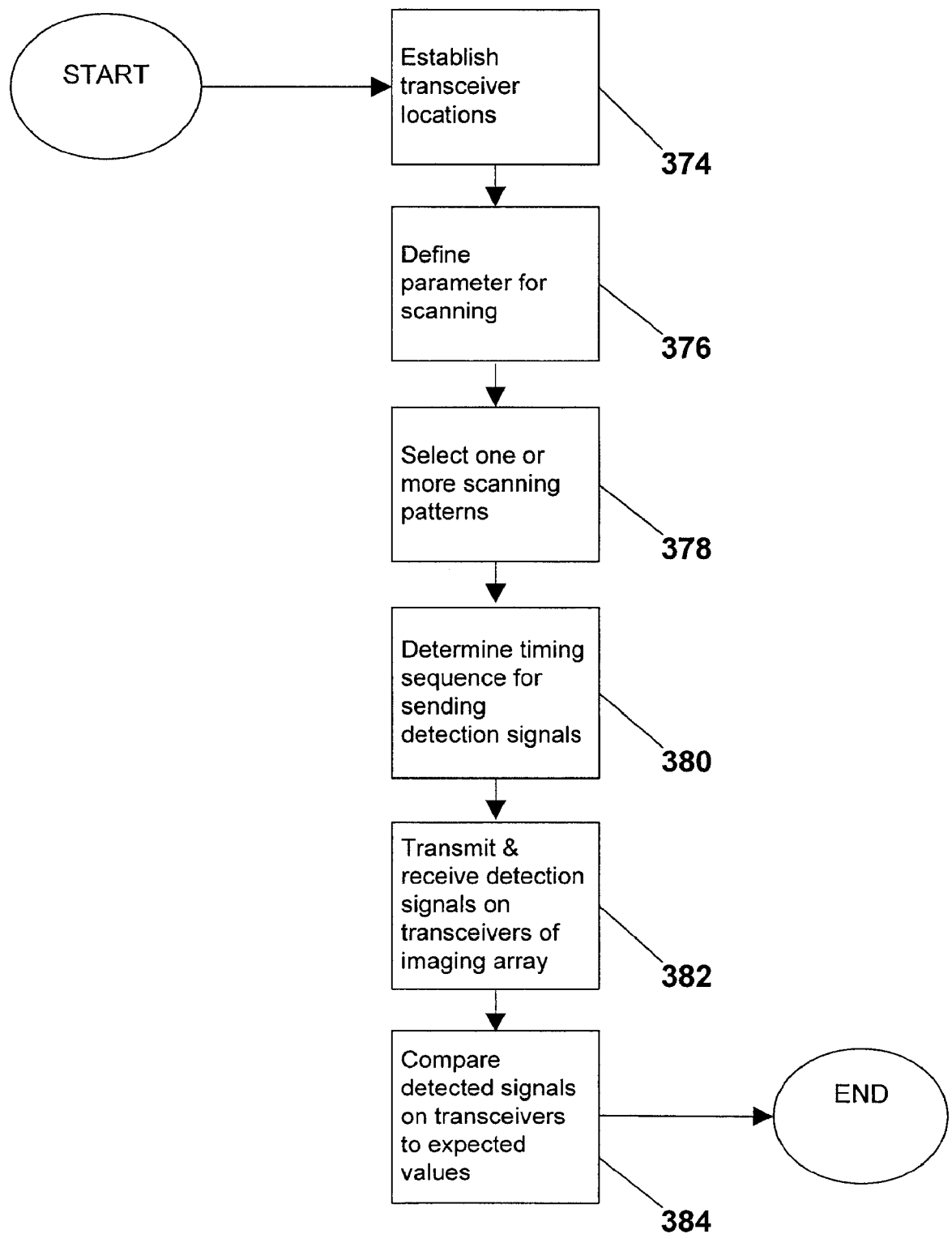
FIG. 15 is a flow chart illustrating a method for operation for an imaging system.

Another aspect of the invention provides methods of operating imaging systems provided in accordance with the invention. For example, as shown in FIG. 15, a method of operating the imaging system provided herein is illustrated that includes a step 374 whereby selected locations of a number of transceivers (18) may be determined for a particular imaging array (12). In one embodiment, an initiation signal may be used to establish the locations of the transceivers in the imaging array. The initiation signal may be a signal sent to the transceivers to establish their locations with regard to one another and a reference point. Another embodiment of the invention includes the step of calculating the location of the transceivers by using external laser measurements and sensing, or by measuring a signal delay across the interconnect network, or using strain gauges which may be employed in either silicon or metal configurations, in order to register the angle and amount of bending flexure across the imaging array. It shall be understood that these and other methods of determining the location of the transceivers are also contemplated herein. In one embodiment, the imaging system may also record the position of the imaging array during a scan to adjust the location of the transceivers. In another embodiment, a series of one or more optical measurements in the imaging array or externally may be taken to register the angle and amount of bending flexure across the imaging array.

At step 376, a selected number of parameters are defined for scanning. In one embodiment of the invention, the parameters may include frequency, power, timing and pattern for the detection signal. The frequency, power and timing may be selected according to the particular area of concern (e.g., type of tissue) and the kind of imaging desired. One or more scanning patterns may be selected at step 378. The scanning patterns may include concentric "circles", line-to-line, point-to-point, point-to-grouping, and grouping-to-point, as described elsewhere herein, e.g., FIGS. 10A-J, however other scanning patterns are also contemplated for use according to these and other aspects of the invention. The kind of scanning patterns that may be used in accordance with the invention may depend upon a number of factors including a particular array configuration being used, the area of concern being scanned, and the type of imaging data desired. For example, an approximate concentric-circular array configuration may be chosen for scanning breast tissue. The pattern selected for a standard annual exam may proceed with transmission of an analysis signal from a single, central transceiver (18A) with reception of the detection signal occurring at one or more transceivers (18B) at one or more locations across the entire placement of transceivers within the concentric-circular array. A series of next steps may be performed to alternately step through the array locations of transceivers to achieve an optimal image by varying angles, frequencies and locations of the analysis signal. Furthermore, in a preferable embodiment of the invention, a rectangular array of transceivers (18) may be chosen for scanning skin tissue. The scanning pattern chosen may proceed from one line of transceivers to a next line of transceivers, which may alternate through several locations in order to approximate the necessary movement of the signals, therefore the angle of the analysis signals and detection signals to achieve the best or optimal imaging data from variable angles of view. In another embodiment of the invention, the placement, pattern and separation of each imaging array may be matched according to the type of imaging being performed. The location of each individual transceiver may be electronically addressed with specified power, timing, and selected distance and/or angle, to create multiple scan lines.

At step 382, detection signals can be transmitted and received by one or more transceivers on the imaging array. In one embodiment, the transmit and receive functions of transceivers may be coordinated and timed for three-dimensional imaging and real-time imaging. In another embodiment, the generation of detection signals and data collection of the imaging system may be electronically controlled for moving the ultrasound signal through a specified pattern of transceivers on the imaging array. The detection signals can be created by each transceiver, and may be controlled so as to not cause interference with another transceiver.

At step 384, the detection signal strength and timing as received from the transceivers can then be compared to an expected transmission. In one embodiment of the invention, selected translations or corrections can be made for the originating signal location when necessary. It should be appreciated that a combination of frequencies may be matched to the tissue to optimize resolution and depth of penetration. The timing and pattern sequence for sending and receiving detection signals may minimize interference, improve resolution and support three-dimensional image creation real-time.

Figure 16:
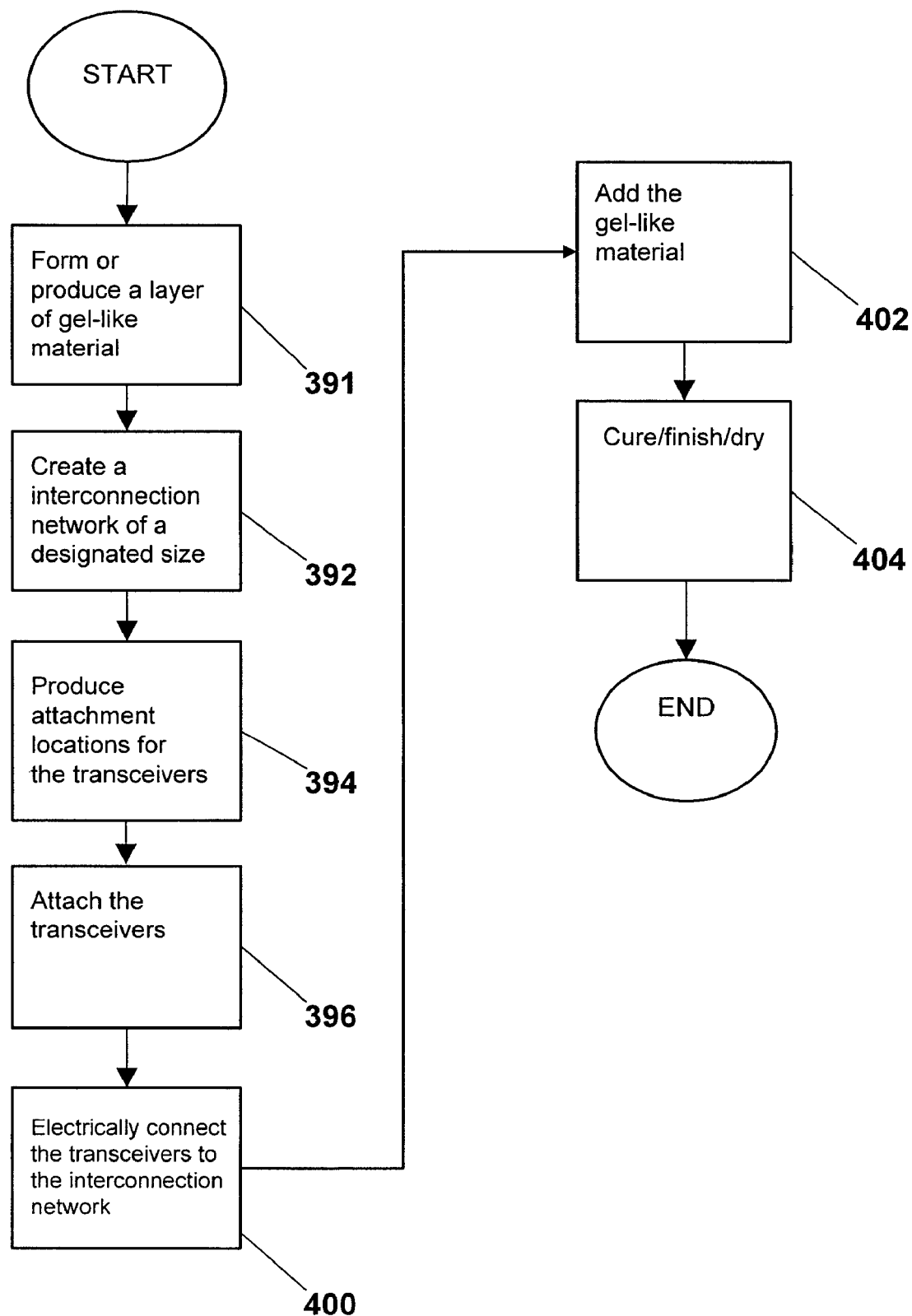
FIG. 16 is a flow chart illustrating a method for manufacturing an embodiment of the imaging system having a carrier base made from a gel-like material.

FIG. 16 illustrates another method of manufacturing an imaging array in accordance with another embodiment of the invention having a carrier base (14E) made from a flex circuit-like and/or a gel-like material, e.g., FIG. 5B. In this implementation, an interconnection network such as those described elsewhere herein may be produced at step 392. Thereafter, at step 396 a selected number of one or more transceivers (18) may be attached. The transceivers may be connected to the electrically conductive network at step 400. Thereafter, the gel-like material may be added at step 402. In one embodiment of the invention, the transceivers and the electrically conductive network may be embedded or encased in gel-like material or in liquid form. In another embodiment, the gel-like transmission layer is separate from and later added to or on top of the surface of the transceivers. At step 404, the gel-like material may be processed, dried and cured. In a preferable embodiment, the processing, drying and curing steps may be performed to achieve a semi-solid consistency. Thereafter, this implementation of the foregoing method is complete.

Figure 17:
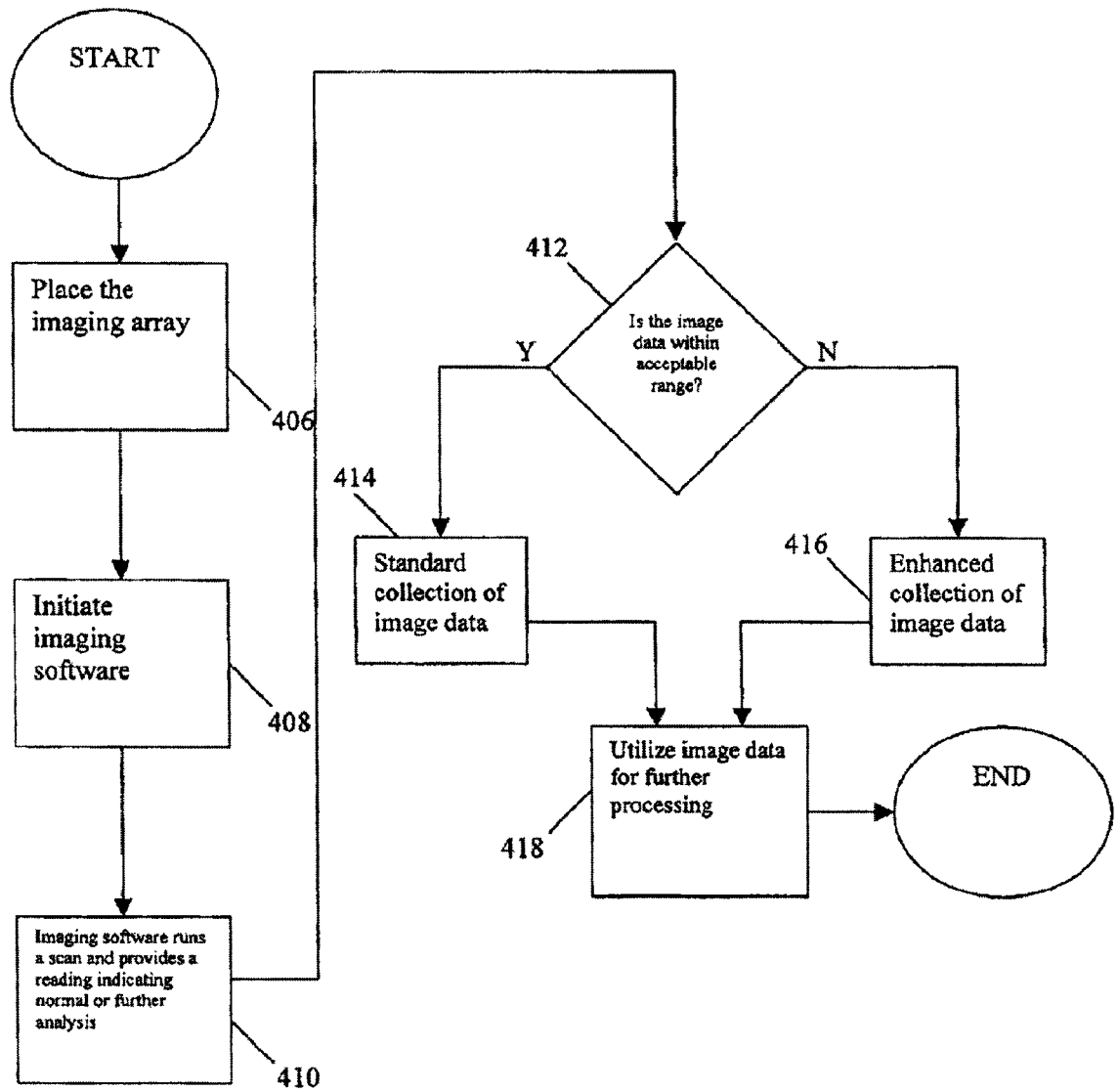
FIG. 17 is a flow chart illustrating the operation of the imaging system.

Referring to FIG. 17, another method is shown for operating an imaging system provided in accordance with the invention. In this implementation, an imaging array is selected and placed over a body area at step 406. As with other imaging array assemblies described elsewhere herein, it should be appreciated that the imaging array may eliminate or not necessitate the use of a liquid transmission gel dispensed onto the patient, through the use of a gel-like material as a carrier material or cover or transmission-aid material, such as those described elsewhere herein with the imaging array. A particular kind of gel-like material may be selected for certain performance characteristics such as having increased transmission efficiencies. In one embodiment of the invention, the imaging array may be placed or fastened in place by use of mechanical means, fasteners or adhesives. The imaging array may be placed at a desired location by applying adhesives directly to a subject or patient. In one embodiment, the imaging array may be placed into position by the use of a registration mark, a locator or a reference point. In another embodiment, registration may be established using a unique imaging feature of the subject tissue itself The imaging array may also be hands-free in operation with one-time, stationary placement. In one embodiment, the imaging array will be configured to be a disposable and/or one-time use array. In another, embodiment only the gel component may be disposable.

At step 408, an operator may initiate a desired imaging software program (80) including those described elsewhere herein. The program can be initiated once an operator selects a frequency range based on the particular end use or application of the imaging system, and upon selection of an imaging routine as defined earlier herein. In one embodiment of the invention, the frequency range may be selected for imaging a specific body tissue. For example, the frequencies used for imaging may be selected in the range of 1-20 MHz. A range of frequencies may be used for pregnancy ultrasounds including a range from 1.6-10 MHz, while in other embodiments of the invention the selected frequencies used for pregnancy ultrasounds may range from between 3 and 7.5 MHz. The range for breast tissue applications may be 3.0-9.0 megahertz. It should be appreciated that desired ranges for various other tissue types may be used and are known in the art.

It should be appreciated that step 406 and step 408 can occur in either order, or that the steps may occur simultaneously or nearly simultaneously. Other steps in the procedures and methods described herein may also be performed in a different sequence as described above unless otherwise specified.

The selected imaging software at step 410 may then run a scan and provide a reading indicating whether the body area scanned register normal readings or whether further analysis is required. For example, a reading may be considered normal when falling within an expected range, or a reading may require or suggest further analysis when it falls outside of an expected range.

The images generated by the computer imaging system can be varied. In one embodiment, the computer system processes the ultrasound data received from the transceivers to produce either a two-dimensional, or a data-slab, or a three-dimensional (3D) image, or real-time 3D (called 4D) as selected by the medical professional and can display an enhanced view of the human body part undergoing examination. In another embodiment, the readings taken can be used to generate a medical ultrasound image, data and information, in a three-dimensional format that can be presented as a translucent data-set to see inside tissue structure for off-line analysis or real-time in a case such as biopsy or surgery. The ultrasound image may be of a part of the human body exposed to transmitted ultrasound signals, and receiving the reflected or transmitted ultrasound signals in the format electronic signal information. The images generated may be characterized as normal as a point of reference for future comparison against images from the same patient over an extended period of time. Furthermore, the readings may be used to render a three-dimensional image that may be used for diagnostic analysis of the patient's body tissue or organ system that has been imaged.

It may be desirable to monitor the movement of the patient or the ultrasound assembly during operation of the imaging arrays herein using apparatus such as an accelerometer. The imaging array may be stationary during readings, however in certain embodiments of the invention the imaging arrays may be moved during operation.

At decision point 412, the imaging software may determine action that should be taken based on whether the reading is within an acceptable range at step 410. If the reading is within a selected range, then the imaging software at step 414 may perform standard collection of image data. The standard collection of image data may preferably store the image data within an image database (78) as described elsewhere herein. If the reading is not within an acceptable range, then the imaging software at step 416 can performs an enhanced collection of image data. In one embodiment of the invention, the enhanced collection of image data may capture additional image data, while in another embodiment, the enhanced collection of image data may capture image data at a higher resolution. The data set for storage can be a complete set or a subset that is statistically chosen to capture critical data points only so as to minimize the amount of computer memory required for storage. The image data stored at step 414 or step 416 may be additional or alternatively stored on a portable data memory storage device (82) as described elsewhere herein or a translator circuit board for data processing or image creation to interface with a third party system. The electronic signals may then be processed and analyzed to produce an image for display and/or the image data may be transmitted to a third party for a variety of purposes including collaboration and remote analysis. In an embodiment of the invention, a selected group of three-dimensional image data may be analyzed statistically against a set of pattern-recognition parameters to provide an adjunctive medical analysis of the body part of interest. The statistically highlighted critical areas of interest may then be selected for storage. Upon completion of step 414 or step 416, the imaging system may utilize the image data for further processing.

In accordance with another aspect of the invention, further processing of the data image may include treating the area of concern. Treating the area of concern include a variety of activities such as providing therapeutic treatment to the area of concern, however other treatments are also contemplated. For example, treatments may include determining concentration of chemicals, radiation dosing, treating an area and therapy such as delivering heat or electromotive movement of medication through skin or other tissue. In addition, further processing of the data image may involve communicating or transmitting the image data or analysis to a medical practitioner, a collaborator, the patient or a remote or local storage. Further processing may also include lensing and/or magnification of the area of concern for additional data. Accordingly, upon completion of step 418, this implementation of the foregoing method is complete. As with other embodiments of the invention described above, a computer system (16) may be used to create a patient code for selected image information for storage, retrieval and comparison of successive ultrasound examinations for any individual or groups of individuals.

It should be appreciated that imaging array systems and related methods of use herein may be used for a variety of imaging applications, such as ultrasound imaging, temperature sensing, infrared, magnetic, or topographical imaging. It should also be appreciated that the imaging arrays may enable a user to make a reading of an area without repositioning the imaging array, and the imaging system may highlight image data deemed important for a particular application, and may support decreased requirements for storage of the images because of the capability of narrowing the readings to areas of greater concern. Preferable embodiments of the invention provide imaging arrays that may be formed of relatively low cost materials and components, e.g., transceivers, transducers, carrier material, suitable for single-time use, or as a disposable item, while in others embodiment provide imaging arrays that may be used multiple or numerous times. In particular, the method of constructions and manufacturing herein can encompass more than just ultrasound transceivers, as noted above but can be equally applicable for measuring or data acquisition on temperature, infrared, optical, or statistical screening of ultrasound data. The data acquisition systems provided herein are not deemed "fixed" and can be modified in various ways. Various components of the system can be tailored according to particular needs reflecting a modular approach such that a probe, imaging or control software, and a corresponding translator board can be manufactured separately but work together to address a specific application for medical data acquisition. At the same time, and as a result, an entire data acquisition system may be variably configured as desired.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A portable ultrasound imaging data acquisition device for sending and receiving ultrasound signals comprising:
    an array configured of a plurality of individually addressable capacitive microfabricated ultrasound transceivers (cMUTs) connected to conductive pathways;
    an interconnection network electrically connected to the plurality of individually addressable cMUTs and the conductive pathways to provide for power and control;
    a tacky cured polymeric semi-solid gel sheet supporting the plurality of cMUTs, the interconnection network and the conductive pathways, the plurality of cMUTs, the interconnection network and the conductive pathways being at least partially embedded within the tacky cured polymeric semi-solid gel sheet; and
    self-powered and controlling electronics assembly, including a computer system, coupled to the conductive pathway to selectively control and operate one or more groups of cMUTs, within the plurality of individually addressable cMUTs to image an area of concern of a subject,
    wherein the electronics assembly, including the computer system, also electronically activates the one or more groups of cMUTs within the plurality of individually addressable cMUTs to send ultrasound analysis signals and/or receive ultrasound acquisition signals;
    wherein at least some of the plurality of individually addressable cMUTs that are electrically connected to the interconnection network and the conductive pathways are configured for both sending ultrasound analysis signals and receiving ultrasound detection signals.

2. The portable ultrasound imaging data acquisition device for sending and receiving ultrasound signals, as set forth in claim 1, further comprising at least one silicon chip for hosting a group of cMUTs, wherein the cMUTs are solid-state structures arranged to provide a one-dimensional or a two-dimensional array.

3. The portable ultrasound imaging data acquisition device for sending and receiving ultrasound signals, as set forth in claim 1, wherein the plurality of cMUTs comprise one or more of the following: silicon, piezoelectric, infrared or electromigration sensors or transceivers.

4. The portable ultrasound imaging data acquisition device for sending and receiving ultrasound signals, as set forth in claim 1, wherein the conductive pathway includes a flex circuit formed of single or multiple levels of metal traces connected to a plurality of integrated circuits (ICs).

5. The portable ultrasound imaging data acquisition device for sending and receiving ultrasound signals, as set forth in claim 1, wherein the controlling electronics assembly is directly connected to or integrally formed with the data acquisition device.

6. The portable ultrasound imaging data acquisition device for sending and receiving ultrasound signals, as set forth in claim 1, wherein the sheet can be configured to provide a flat, curved or conical structure that is rigid, flexible, or conformable.

7. The portable ultrasound imaging data acquisition device for sending and receiving ultrasound signals, as set forth in claim 1, wherein the sheet is formed with as a square shape three inches by three inches, or circular shape four to six inches in diameter, or a strip configuration two inches by four inches, which is selected based on the type of imaging to be performed, and further customized according to a region to be imaged by incorporating cut-outs or slits for best conformability.

8. The portable ultrasound imaging data acquisition device for sending and receiving ultrasound signals, as set forth in claim 1, wherein the portable ultrasound imaging data acquisition device is further configured for acquiring images during one or more of the following procedures: breast tissue imaging, surgical guidance, skin procedures and emergency response.

9. The portable ultrasound imaging data acquisition device for sending and receiving ultrasound signals, as set forth in claim 1, wherein the data acquisition device is constructed from one or more single-use materials in a configuration that is disposable.

10. The portable ultrasound imaging data acquisition device for sending and receiving ultrasound signals, as set forth in claim 1, wherein the data acquisition device can be configured for operator-independent stationary hands-free data acquisition.

11. The portable ultrasound imaging data acquisition device for sending and receiving ultrasound signals, as set forth in claim 1, further comprising an electronics board and computer processing system operatively coupled to the data acquisition device to manipulate, store and prepare data into an ultrasound data set, or a 2D, 3D, or 4D image.

* * * * *